(12) United States Patent
Laird, Jr. et al.

(10) Patent No.: US 12,343,051 B2
(45) Date of Patent: Jul. 1, 2025

(54) DISTAL TIBIAL PLATING SYSTEM

(71) Applicant: GLOBUS MEDICAL, INC., Audubon, PA (US)

(72) Inventors: David Laird, Jr., Brandamore, PA (US); Alex Bada, Phoenixville, PA (US); Andrew Davison, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 440 days.

(21) Appl. No.: 17/558,679

(22) Filed: Dec. 22, 2021

(65) Prior Publication Data
US 2022/0110665 A1    Apr. 14, 2022

Related U.S. Application Data

(63) Continuation of application No. 15/910,041, filed on Mar. 2, 2018, now Pat. No. 11,224,468.

(51) Int. Cl.
| | |
|---|---|
| *A61B 17/80* | (2006.01) |
| *A61B 17/04* | (2006.01) |
| *A61B 17/84* | (2006.01) |
| *A61B 17/68* | (2006.01) |

(52) U.S. Cl.
CPC ...... *A61B 17/8014* (2013.01); *A61B 17/0401* (2013.01); *A61B 17/8057* (2013.01); *A61B 17/8061* (2013.01); *A61B 17/8085* (2013.01); *A61B 17/848* (2013.01); *A61B 2017/681* (2013.01)

(58) Field of Classification Search
CPC ...................... A61B 17/80–17/8095
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,463,148 | A | 8/1969 | Treace |
| 3,510,923 | A | 5/1970 | Blake |
| 3,695,259 | A | 10/1972 | Yost |
| 4,219,015 | A | 8/1980 | Steinemann |
| 4,493,317 | A | 1/1985 | Klaue |
| 4,524,765 | A | 6/1985 | de Zbikowski |
| 4,651,724 | A | 3/1987 | Berentey et al. |
| 4,781,183 | A | 11/1988 | Casey et al. |
| 4,867,144 | A | 9/1989 | Karas et al. |
| 4,896,661 | A | 1/1990 | Bogert et al. |
| 4,966,599 | A | 10/1990 | Pollock |
| 5,002,544 | A | 3/1991 | Klaue et al. |

(Continued)

FOREIGN PATENT DOCUMENTS

| | | |
|---|---|---|
| EP | 3202348 A1 | 8/2017 |
| JP | 2007-518537 A | 7/2007 |
| WO | WO-2017035302 A1 * 3/2017 ......... A61B 17/1725 |

*Primary Examiner* — Zade Coley

(57) ABSTRACT

Bone plates for engaging bone members are described herein. The bone plates can receive one or more screws to secure the bone plates to an underlying bone member. The one or more screws can be inserted into bone plate holes that can be considered locking or non-locking. The bone plates described herein can have particular combinations of locking and/or non-locking holes. Additional bone plate holes can be used to accept sutures, K-wire, or other instrumentation.

18 Claims, 19 Drawing Sheets

(56) References Cited

U.S. PATENT DOCUMENTS

| | | | |
|---|---|---|---|
| 5,041,114 | A | 8/1991 | Chapman et al. |
| 5,151,103 | A | 9/1992 | Tepic et al. |
| 5,259,398 | A | 11/1993 | Vrespa |
| 5,364,399 | A | 11/1994 | Lowery et al. |
| 5,372,598 | A | 12/1994 | Luhr et al. |
| 5,423,826 | A | 6/1995 | Coates et al. |
| 5,601,553 | A | 2/1997 | Trebing et al. |
| 5,676,667 | A | 10/1997 | Hausman |
| 5,709,686 | A | 1/1998 | Talos et al. |
| 5,718,704 | A | 2/1998 | Medoff |
| 5,746,742 | A | 5/1998 | Runciman et al. |
| 5,766,176 | A | 6/1998 | Duncan |
| 5,779,706 | A | 7/1998 | Tschakaloff |
| 5,785,712 | A | 7/1998 | Runciman et al. |
| 5,938,664 | A | 8/1999 | Winquist et al. |
| 5,980,540 | A | 11/1999 | Bruce |
| 6,001,099 | A | 12/1999 | Huebner |
| 6,071,291 | A | 6/2000 | Forst et al. |
| 6,096,040 | A * | 8/2000 | Esser ............... A61B 17/8061 606/280 |
| 6,107,718 | A | 8/2000 | Schustek et al. |
| 6,152,927 | A | 11/2000 | Farris et al. |
| 6,206,881 | B1 | 3/2001 | Frigg et al. |
| 6,283,969 | B1 | 9/2001 | Grusin et al. |
| 6,309,393 | B1 | 10/2001 | Tepic et al. |
| 6,322,562 | B1 | 11/2001 | Wolter |
| 6,364,882 | B1 | 4/2002 | Orbay |
| D458,683 | S | 6/2002 | Bryant et al. |
| D458,684 | S | 6/2002 | Bryant et al. |
| 6,533,786 | B1 | 3/2003 | Needham et al. |
| D479,331 | S | 9/2003 | Pike et al. |
| 6,623,486 | B1 | 9/2003 | Weaver et al. |
| 6,669,700 | B1 | 12/2003 | Farris et al. |
| 6,669,701 | B2 | 12/2003 | Steiner et al. |
| 6,712,820 | B2 | 3/2004 | Orbay |
| 6,719,759 | B2 | 4/2004 | Wagner et al. |
| 6,730,091 | B1 | 5/2004 | Pfefferle et al. |
| 6,866,665 | B2 | 3/2005 | Orbay |
| 6,955,677 | B2 | 10/2005 | Dahners |
| 6,974,461 | B1 | 12/2005 | Wolter |
| 7,001,387 | B2 | 2/2006 | Farris et al. |
| 7,063,701 | B2 | 6/2006 | Michelson |
| 7,090,676 | B2 | 8/2006 | Huebner et al. |
| 7,128,744 | B2 | 10/2006 | Weaver et al. |
| 7,137,987 | B2 | 11/2006 | Patterson et al. |
| 7,153,309 | B2 | 12/2006 | Huebner et al. |
| 7,179,260 | B2 | 2/2007 | Gerlach et al. |
| 7,250,053 | B2 | 7/2007 | Orbay |
| 7,294,130 | B2 | 11/2007 | Orbay |
| 7,322,983 | B2 | 1/2008 | Harris |
| 7,341,589 | B2 | 3/2008 | Weaver et al. |
| 7,344,538 | B2 | 3/2008 | Myerson et al. |
| 7,354,441 | B2 | 4/2008 | Frigg |
| 7,604,657 | B2 * | 10/2009 | Orbay ............... A61B 17/8061 606/280 |
| 7,635,381 | B2 | 12/2009 | Orbay |
| 7,637,928 | B2 | 12/2009 | Fernandez |
| 7,655,029 | B2 | 2/2010 | Niedernberger et al. |
| 7,655,047 | B2 | 2/2010 | Swords |
| 7,695,472 | B2 | 4/2010 | Young |
| 7,722,653 | B2 | 5/2010 | Young et al. |
| 7,740,648 | B2 | 6/2010 | Young et al. |
| D622,853 | S | 8/2010 | Raven, III |
| 7,771,457 | B2 | 8/2010 | Kay et al. |
| 7,776,076 | B2 | 8/2010 | Grady, Jr. et al. |
| 7,857,838 | B2 | 12/2010 | Orbay |
| 7,867,260 | B2 | 1/2011 | Meyer et al. |
| 7,867,261 | B2 | 1/2011 | Sixto, Jr. et al. |
| 7,875,062 | B2 | 1/2011 | Lindemann et al. |
| 7,905,910 | B2 * | 3/2011 | Gerlach ............ A61B 17/8014 606/915 |
| 7,909,858 | B2 | 3/2011 | Gerlach et al. |
| 7,951,178 | B2 | 5/2011 | Jensen |
| 7,951,179 | B2 | 5/2011 | Matityahu |
| 7,976,570 | B2 | 7/2011 | Wagner et al. |
| D643,121 | S | 8/2011 | Millford et al. |
| D646,785 | S | 10/2011 | Milford |
| 8,043,297 | B2 | 10/2011 | Grady, Jr. et al. |
| 8,057,520 | B2 | 11/2011 | Ducharme et al. |
| 8,062,296 | B2 | 11/2011 | Orbay et al. |
| 8,100,953 | B2 | 1/2012 | White et al. |
| 8,114,081 | B2 | 2/2012 | Kohut et al. |
| 8,118,846 | B2 | 2/2012 | Leither et al. |
| 8,118,848 | B2 | 2/2012 | Ducharme et al. |
| 8,167,918 | B2 | 5/2012 | Strnad et al. |
| 8,177,820 | B2 | 5/2012 | Anapliotis et al. |
| 8,246,661 | B2 | 8/2012 | Beutter et al. |
| 8,252,032 | B2 | 8/2012 | White et al. |
| 8,257,403 | B2 | 9/2012 | Den Hartog et al. |
| 8,257,405 | B2 | 9/2012 | Haidukewych et al. |
| 8,257,406 | B2 | 9/2012 | Kay et al. |
| 8,262,707 | B2 | 9/2012 | Huebner et al. |
| 8,317,842 | B2 | 11/2012 | Graham et al. |
| 8,323,321 | B2 | 12/2012 | Gradl |
| 8,337,535 | B2 | 12/2012 | White et al. |
| 8,343,155 | B2 | 1/2013 | Fisher et al. |
| 8,382,807 | B2 | 2/2013 | Austin et al. |
| 8,394,098 | B2 | 3/2013 | Orbay et al. |
| 8,394,130 | B2 | 3/2013 | Orbay et al. |
| 8,398,685 | B2 | 3/2013 | McGarity et al. |
| 8,403,966 | B2 | 3/2013 | Ralph et al. |
| 8,419,775 | B2 | 4/2013 | Orbay et al. |
| 8,444,679 | B2 | 5/2013 | Ralph et al. |
| 8,506,608 | B2 | 8/2013 | Cerynik et al. |
| 8,512,384 | B2 | 8/2013 | Beutter et al. |
| 8,512,385 | B2 | 8/2013 | White et al. |
| 8,518,090 | B2 | 8/2013 | Huebner et al. |
| 8,523,862 | B2 | 9/2013 | Murashko, Jr. |
| 8,523,921 | B2 | 9/2013 | Horan et al. |
| 8,551,095 | B2 | 10/2013 | Fritzinger et al. |
| 8,551,143 | B2 | 10/2013 | Norris et al. |
| 8,568,462 | B2 | 10/2013 | Sixto, Jr. et al. |
| 8,574,268 | B2 | 11/2013 | Chan et al. |
| 8,597,334 | B2 | 12/2013 | Mocanu |
| 8,603,147 | B2 | 12/2013 | Sixto, Jr. et al. |
| 8,617,224 | B2 | 12/2013 | Kozak et al. |
| 8,632,574 | B2 | 1/2014 | Kortenbach et al. |
| 8,641,744 | B2 | 2/2014 | Weaver et al. |
| 8,728,126 | B2 | 5/2014 | Steffen |
| 8,740,905 | B2 | 6/2014 | Price et al. |
| 8,747,442 | B2 | 6/2014 | Orbay et al. |
| 8,764,808 | B2 | 7/2014 | Gonzalez-Hernandez |
| 8,777,998 | B2 | 7/2014 | Daniels et al. |
| 8,790,376 | B2 | 7/2014 | Fritzinger et al. |
| 8,808,333 | B2 | 8/2014 | Kuster et al. |
| 8,808,334 | B2 * | 8/2014 | Strnad ............... A61B 17/80 606/280 |
| 8,834,537 | B2 | 9/2014 | Castanada et al. |
| 8,852,246 | B2 | 10/2014 | Hansson |
| 8,852,249 | B2 | 10/2014 | Ahrens et al. |
| 8,864,802 | B2 * | 10/2014 | Schwager ......... A61B 17/8057 606/286 |
| 8,870,931 | B2 | 10/2014 | Dahners et al. |
| 8,888,825 | B2 | 11/2014 | Batsch et al. |
| 8,906,076 | B2 | 12/2014 | Mocanu et al. |
| 8,911,482 | B2 | 12/2014 | Lee et al. |
| 8,926,675 | B2 | 1/2015 | Leung et al. |
| 8,940,026 | B2 | 1/2015 | Hilse et al. |
| 8,940,028 | B2 | 1/2015 | Austin et al. |
| 8,940,029 | B2 | 1/2015 | Leung et al. |
| 8,951,291 | B2 | 2/2015 | Impellizzeri |
| 8,968,368 | B2 | 3/2015 | Tepic |
| 8,979,866 | B2 | 3/2015 | Patel et al. |
| 9,011,457 | B2 | 4/2015 | Grady, Jr. et al. |
| 9,023,052 | B2 | 5/2015 | Lietz et al. |
| 9,050,151 | B2 | 6/2015 | Schilter |
| 9,072,555 | B2 | 7/2015 | Michel |
| 9,107,678 | B2 | 8/2015 | Murner et al. |
| 9,107,711 | B2 | 8/2015 | Hainard |
| 9,107,713 | B2 * | 8/2015 | Horan ............... A61B 17/8061 |
| 9,107,718 | B2 | 8/2015 | Isch |
| 9,113,970 | B2 | 8/2015 | Lewis et al. |
| 9,149,310 | B2 | 10/2015 | Fritzinger et al. |
| 9,161,791 | B2 | 10/2015 | Frigg |

(56) References Cited

U.S. PATENT DOCUMENTS

| | | |
|---|---|---|
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,545,277 B2 | 1/2017 | Wolf et al. |
| 9,579,133 B2 | 2/2017 | Guthlein |
| 9,743,966 B2* | 8/2017 | Horan .............. A61B 17/8061 |
| 9,814,504 B2 | 11/2017 | Ducharme et al. |
| 10,687,874 B2* | 6/2020 | Langdale ........... A61B 17/7241 |
| 10,856,920 B2* | 12/2020 | Tiongson .......... A61B 17/8061 |
| 2002/0045901 A1 | 4/2002 | Wagner et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0182406 A1* | 8/2005 | Orbay ................. A61B 17/8047 |
| | | 606/232 |
| 2005/0187551 A1 | 8/2005 | Orbay et al. |
| 2006/0149265 A1 | 7/2006 | James et al. |
| 2006/0173458 A1* | 8/2006 | Forstein ............ A61B 17/1728 |
| | | 606/281 |
| 2006/0241607 A1 | 10/2006 | Myerson et al. |
| 2007/0270849 A1 | 11/2007 | Orbay et al. |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0143825 A1 | 6/2009 | Graham et al. |
| 2009/0198285 A1 | 8/2009 | Raven, III |
| 2009/0228010 A1 | 9/2009 | Gonzalez-Hernandez et al. |
| 2009/0248084 A1 | 10/2009 | Hintermann |
| 2009/0281543 A1 | 11/2009 | Orbay et al. |
| 2009/0312760 A1 | 12/2009 | Forstein et al. |
| 2010/0030277 A1 | 2/2010 | Haidukewych et al. |
| 2010/0057086 A1 | 3/2010 | Price et al. |
| 2010/0179599 A1* | 7/2010 | Derouet ............ A61B 17/1735 |
| | | 606/301 |
| 2010/0274247 A1 | 10/2010 | Grady, Jr. et al. |
| 2011/0218580 A1 | 9/2011 | Schwager et al. |
| 2012/0197303 A1 | 8/2012 | King et al. |
| 2012/0321328 A1 | 12/2012 | Baker et al. |
| 2013/0018426 A1 | 1/2013 | Tsai et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0245695 A1* | 9/2013 | Bordeaux .......... A61B 17/8066 |
| | | 606/280 |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1* | 11/2015 | Horan ................. A61B 17/8057 |
| | | 606/281 |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0074081 A1 | 3/2016 | Weaver et al. |
| 2016/0166297 A1* | 6/2016 | Mighell ............. A61B 17/8019 |
| | | 623/20.14 |
| 2016/0166298 A1* | 6/2016 | Mighell ............. A61B 17/0401 |
| | | 606/280 |
| 2016/0262814 A1 | 9/2016 | Wainscott |
| 2016/0278828 A1 | 9/2016 | Ragghianti |
| 2016/0031018 A1 | 10/2016 | Kazanovicz et al. |
| 2016/0310183 A1 | 10/2016 | Shah et al. |
| 2017/0042596 A9* | 2/2017 | Mighell ............. A61B 17/8061 |
| 2017/0056081 A1* | 3/2017 | Langdale ............. A61B 17/72 |
| 2017/0156767 A1* | 6/2017 | Chaudot ............ A61B 17/8061 |
| 2017/0296248 A1 | 10/2017 | Paulisch et al. |
| 2018/0049784 A1 | 2/2018 | Gault et al. |

\* cited by examiner

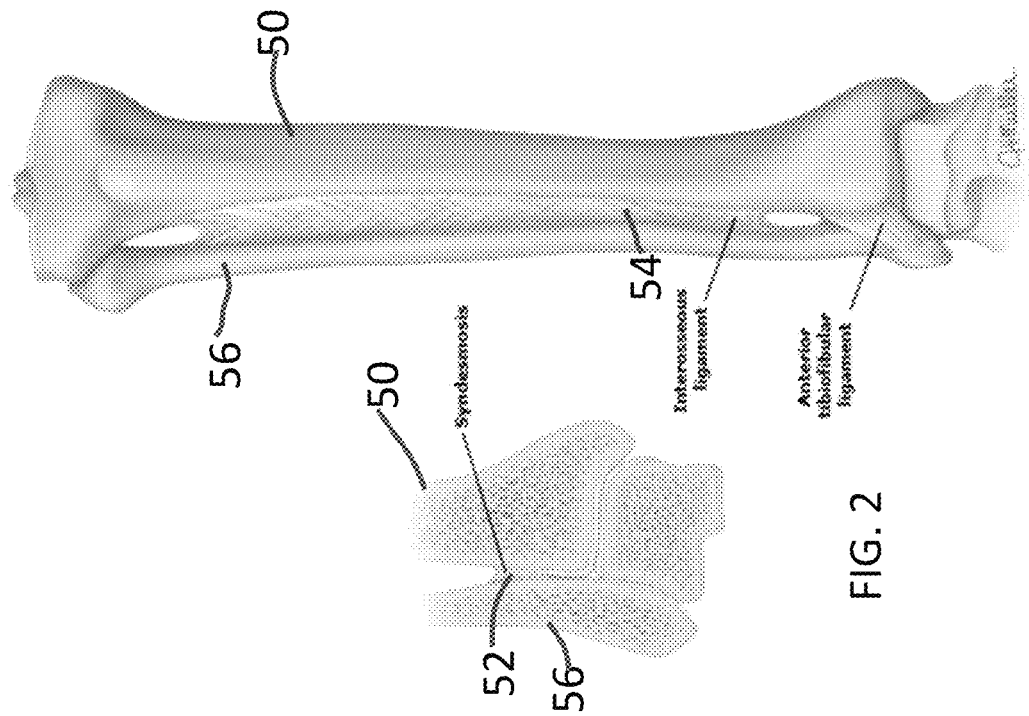
FIG. 2A
FIG. 2
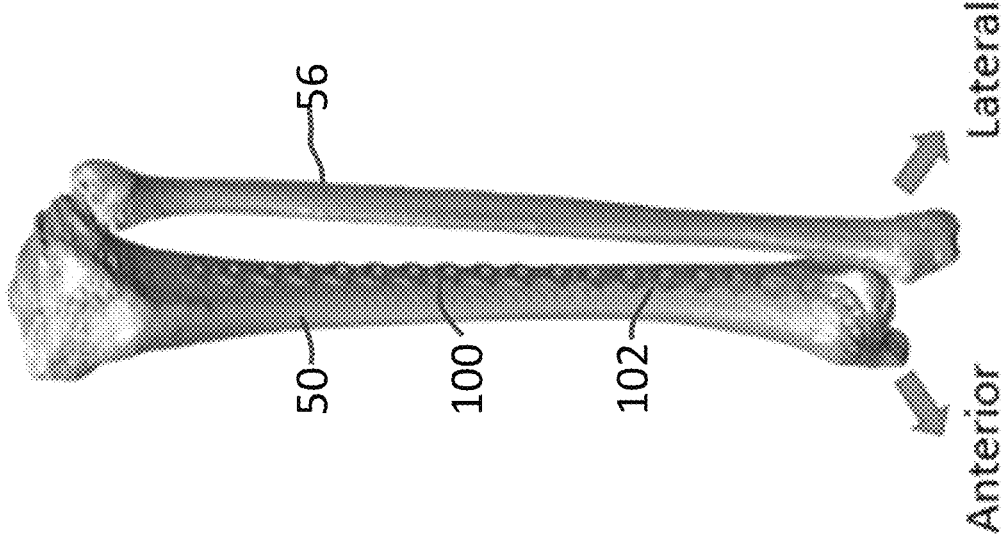
FIG. 1

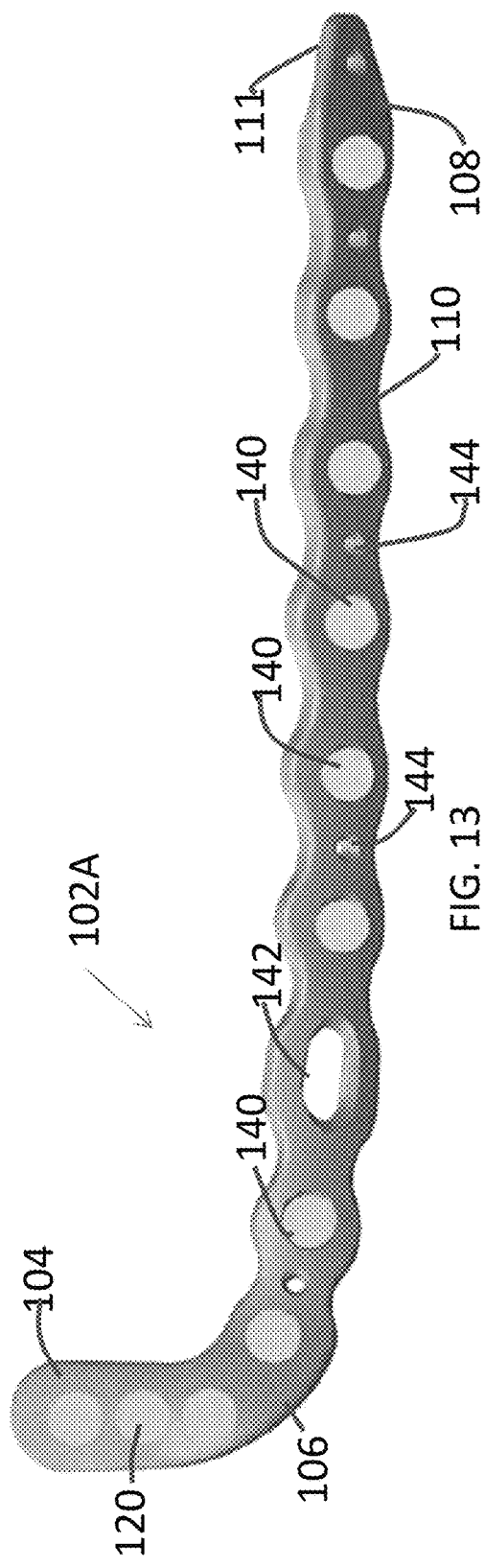
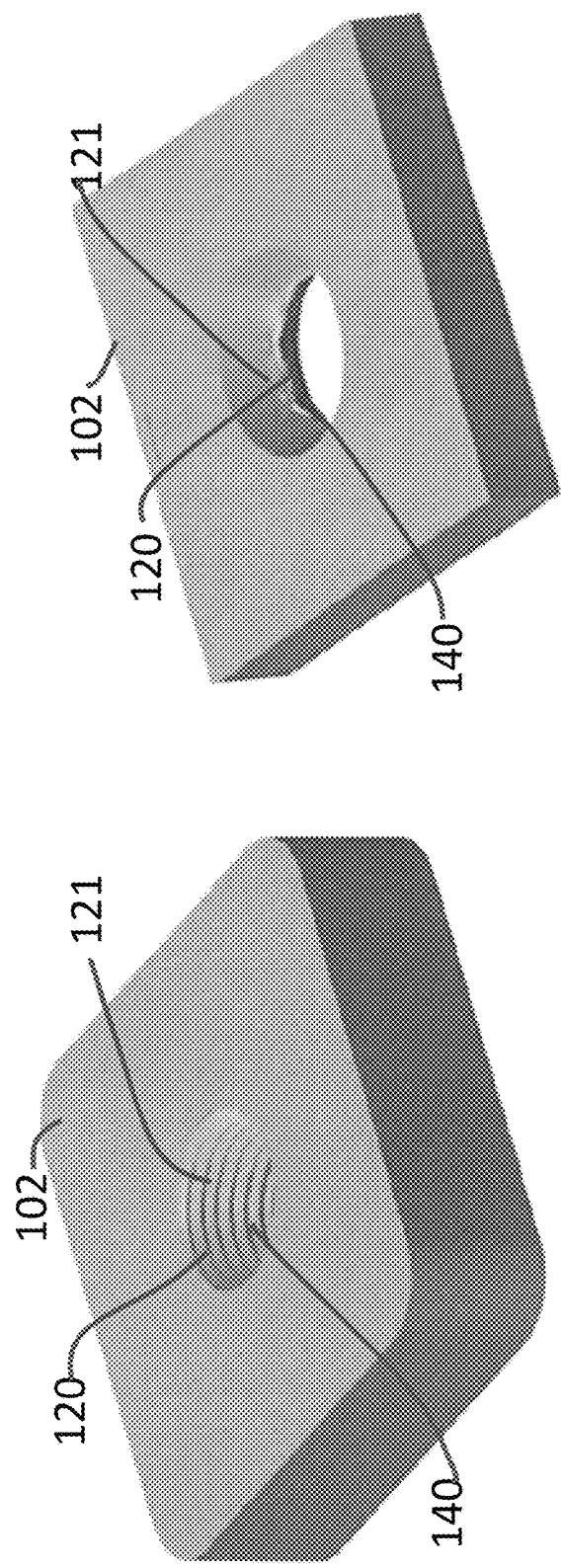
FIG. 13
FIG. 14
FIG. 15

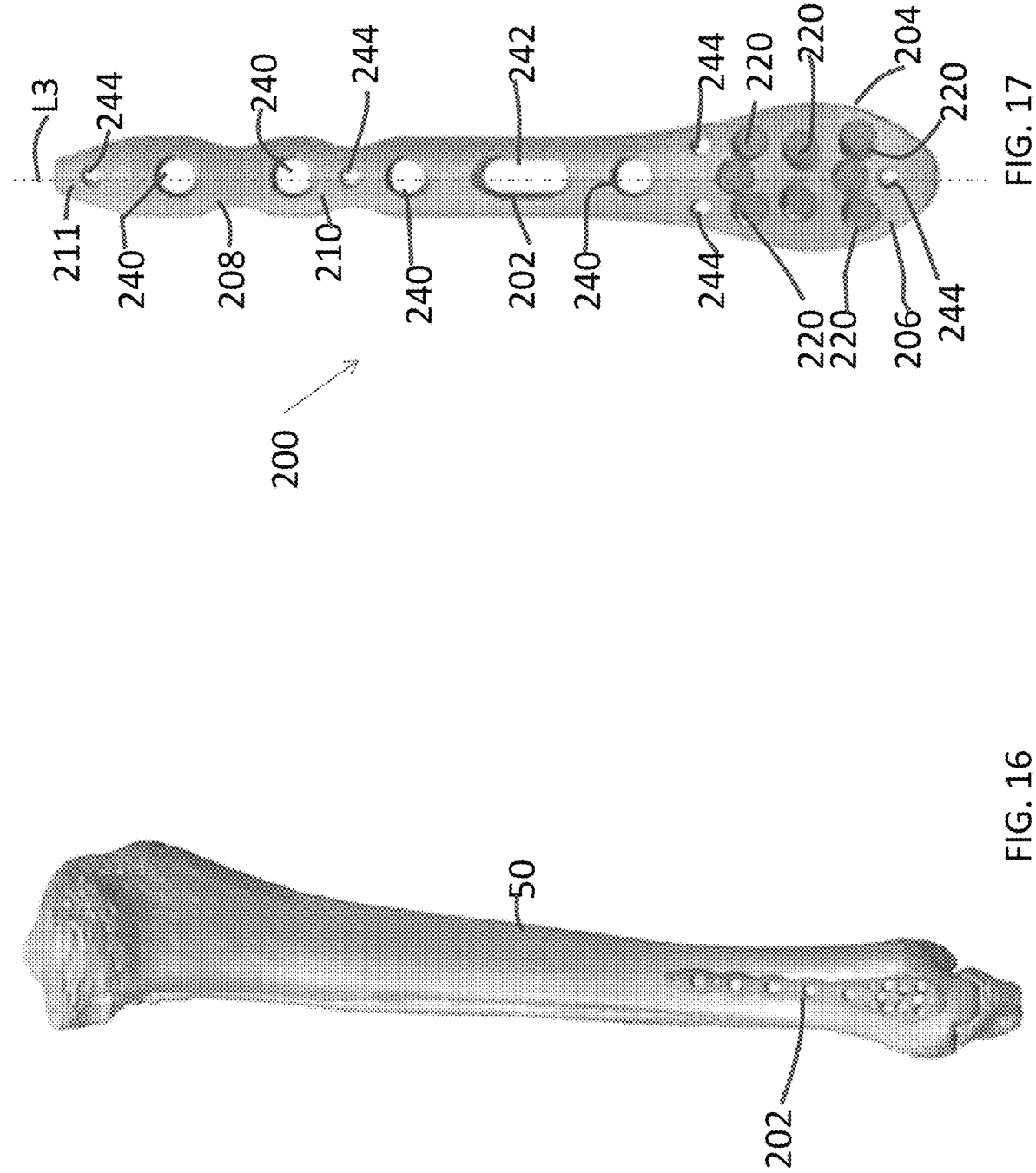

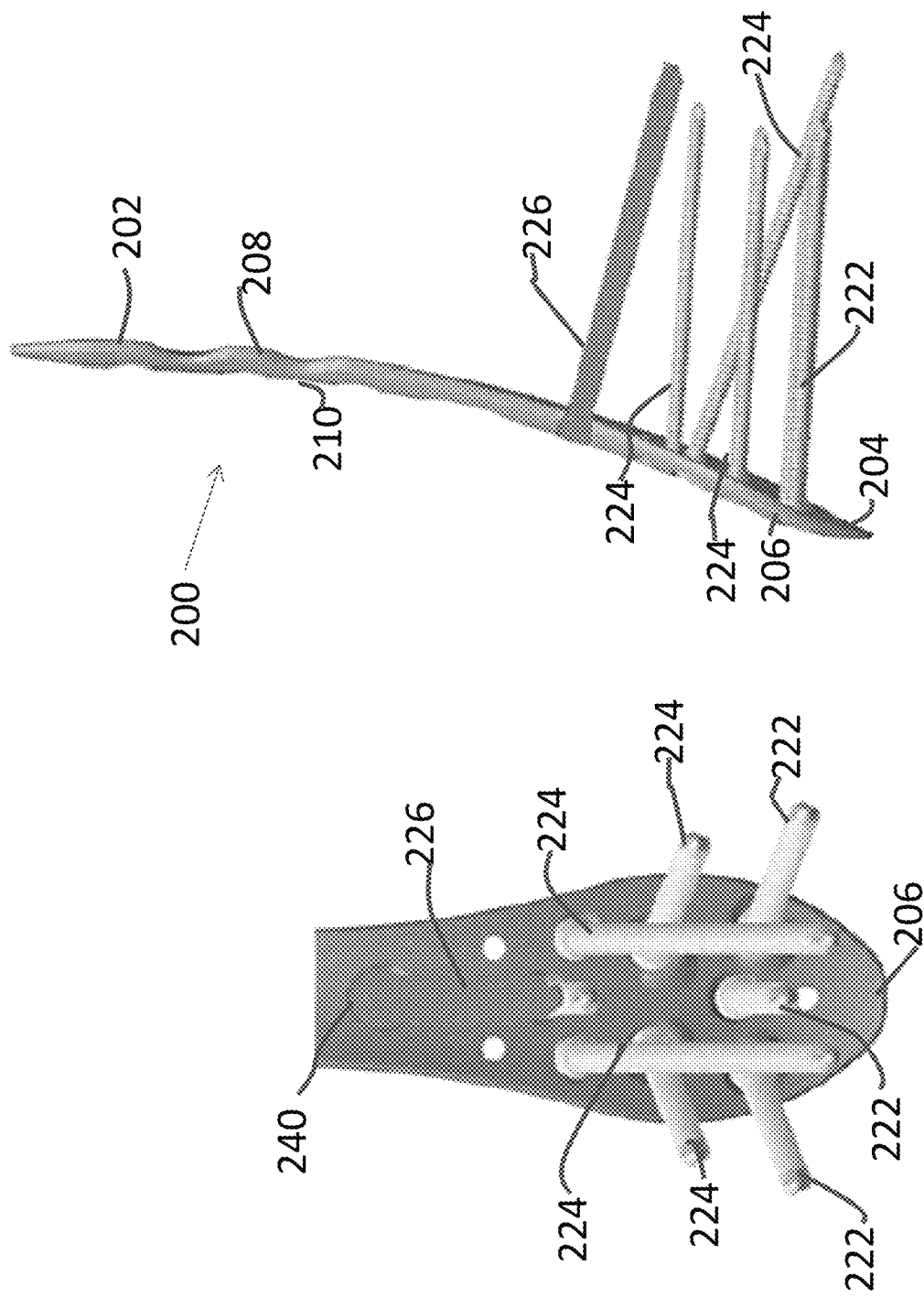

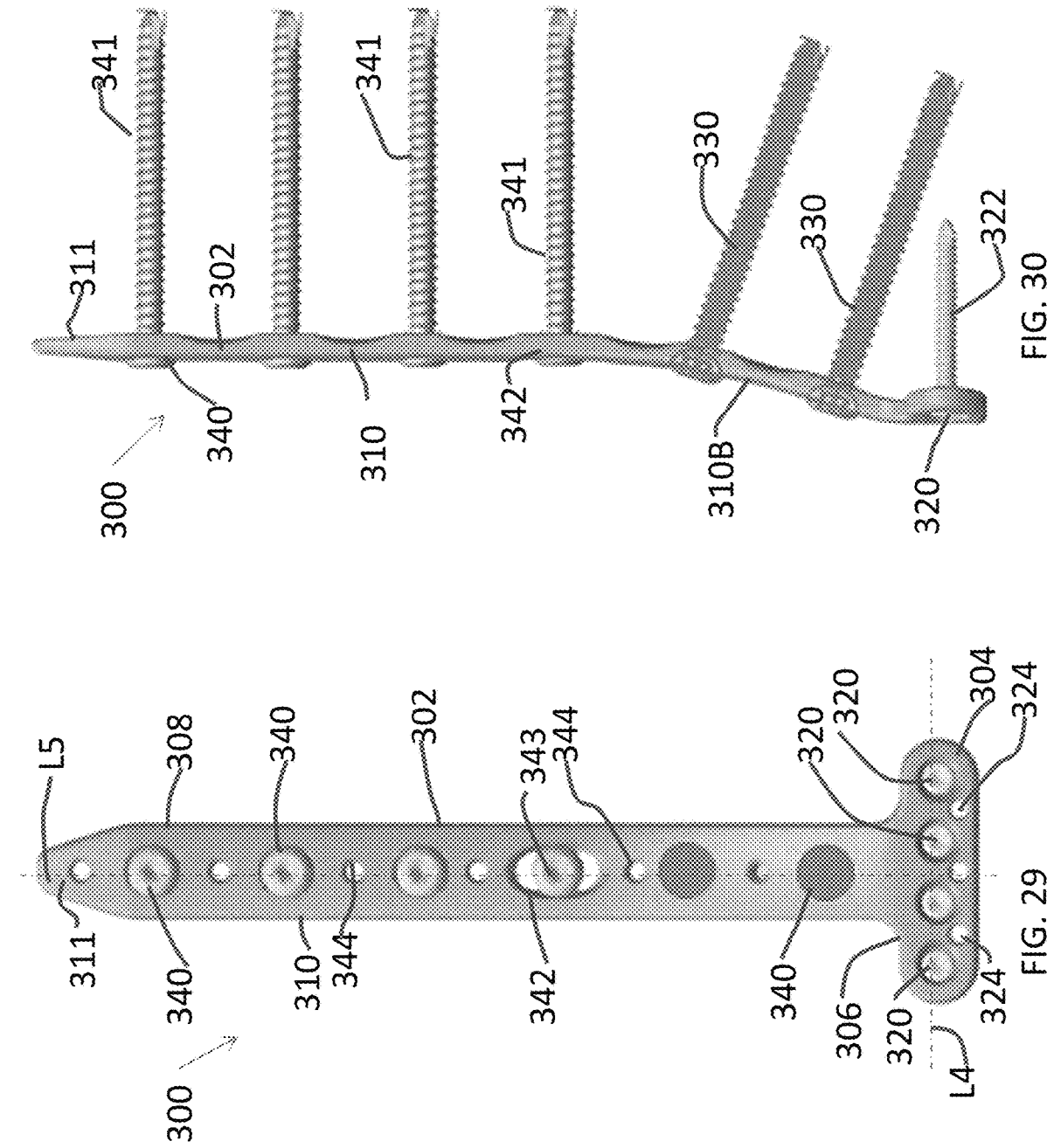

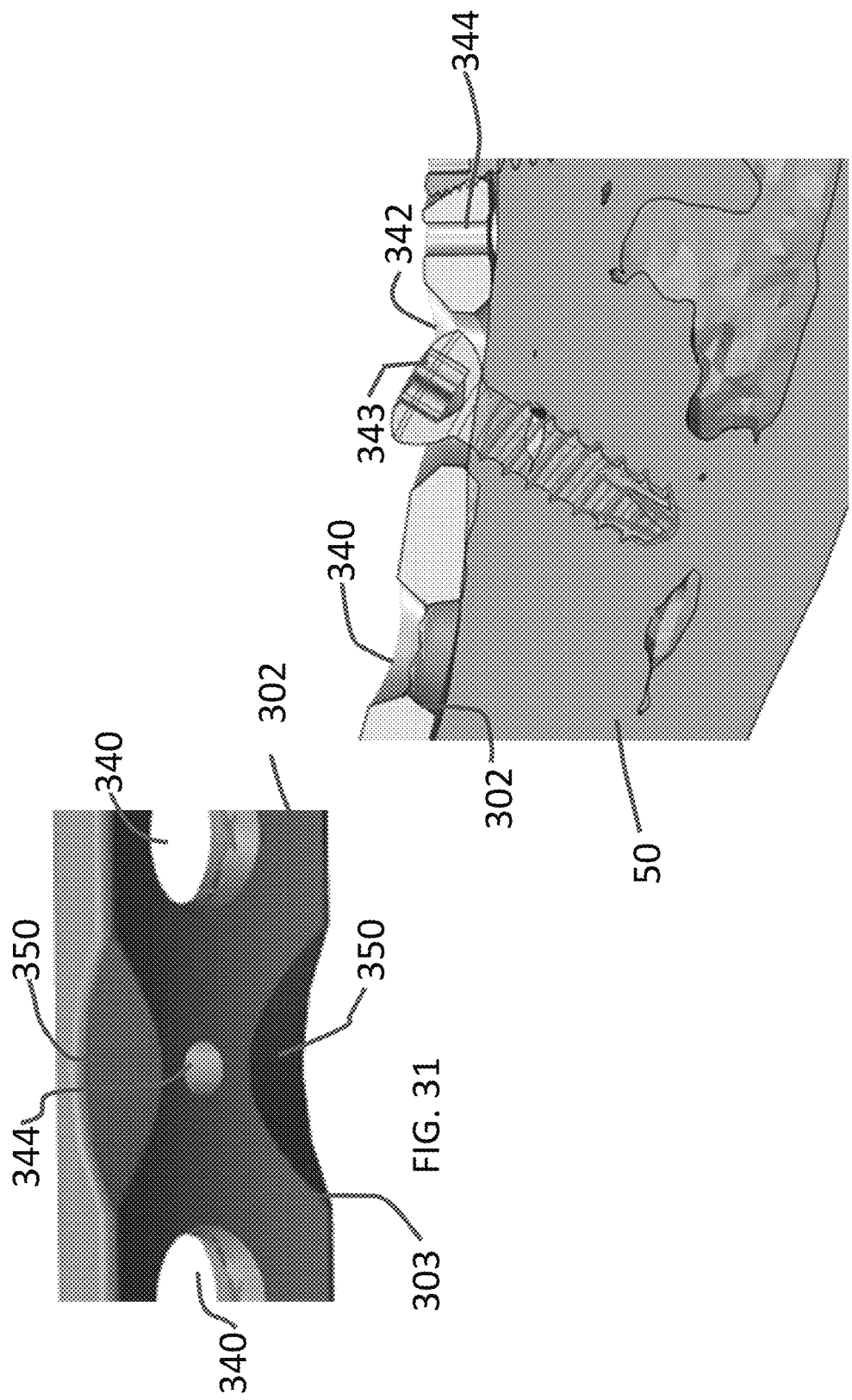

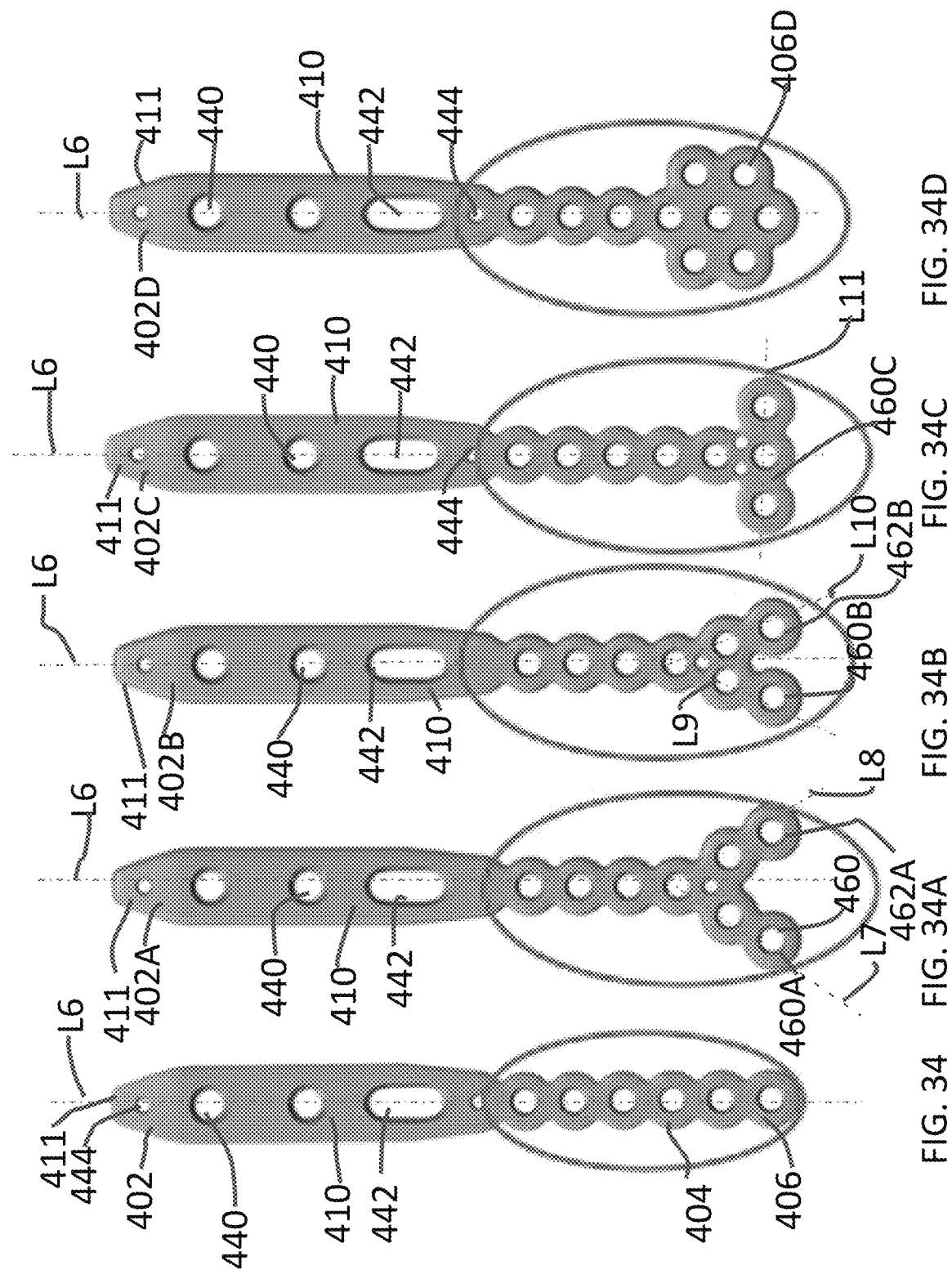

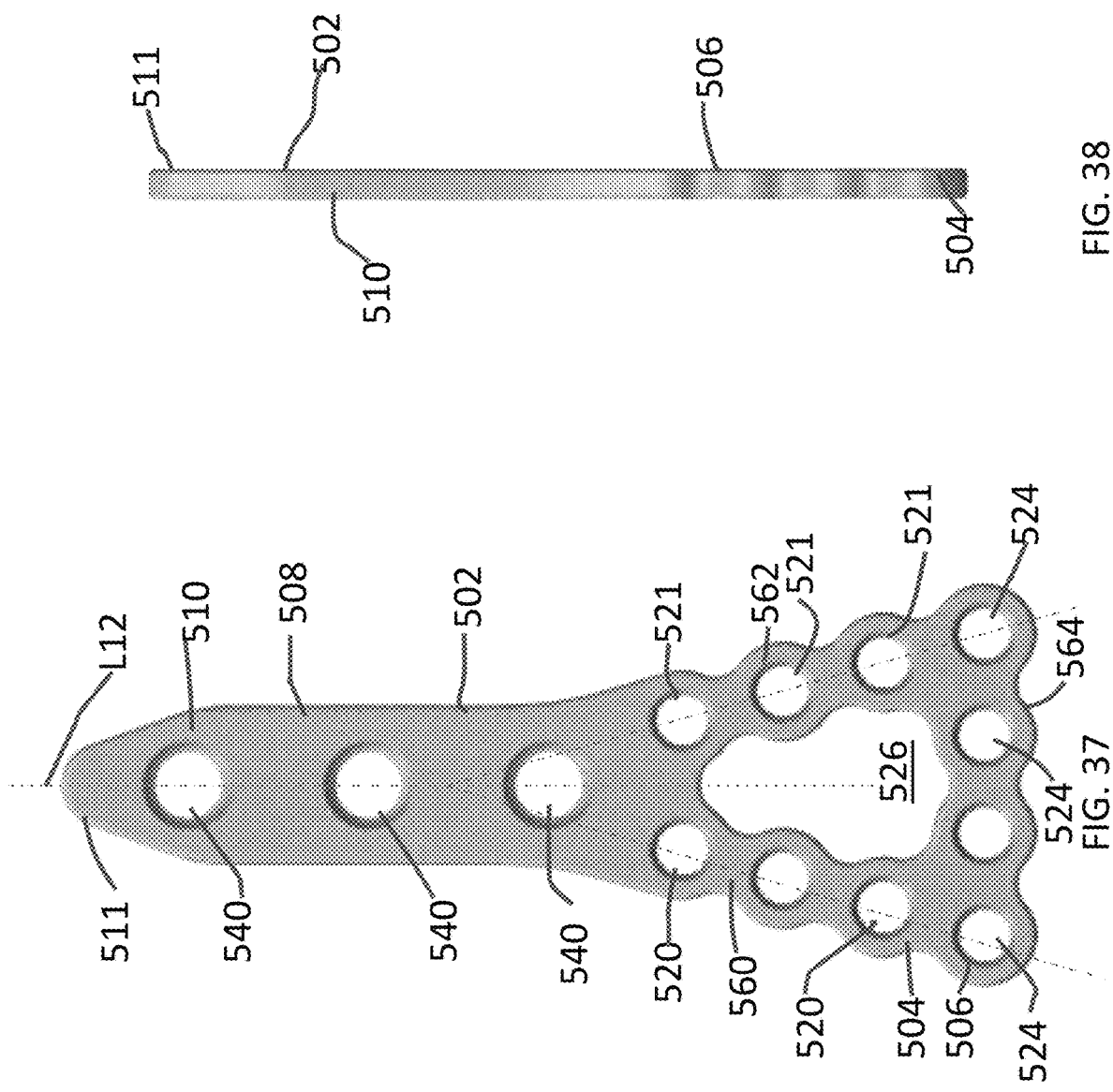

DISTAL TIBIAL PLATING SYSTEM

CROSS-REFERENCE TO RELATED APPLICATIONS

The present application is a continuation of U.S. patent application Ser. No. 15/910,041, filed Mar. 2, 2018, which is incorporated herein by reference in its entirety.

FIELD OF THE INVENTION

The present disclosure relates to surgical devices, systems, and methods, and more particularly, stabilization systems including plates, for example, for trauma applications.

BACKGROUND OF THE INVENTION

Bone fractures can be healed using plating systems. During treatment, one or more screws are placed on either side of a fracture, thereby causing compression and healing of the fracture. There is a need for improved plating systems as well as mechanisms for accurate use of the plating systems.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with the application, a system for treating a fracture in a bone is provided. In some embodiments, the system comprises a bone plate configured to engage the bone. The bone plate includes an inferior end having a base portion extending along a first axis. The base portion comprises a first row of holes and a second row of holes for receiving one or more fasteners therein. A superior end has a shaft portion connected to the base portion. The shaft portion extends along a second axis, different from the first axis and comprises at least one additional hole for receiving a fastener therein. At least one fastener is received in the base portion and is positioned in the first row of holes or second row of holes. Also, at least one additional fastener is also received in the shaft portion and is positioned in the at least one additional hole.

In other embodiments, the system comprises a bone plate configured to engage the bone. The bone plate comprises an inferior end having a base portion. The base portion has a first type of hole formed therethrough and a second type of hole formed therethrough. A superior end has a shaft portion. The shaft portion has a third type of hole formed therethrough and a fourth type of hole formed therethrough. At least one fastener is received in the base portion and positioned in the first type of hole, wherein the at least one fastener is non-threaded. At least one additional fastener is received in the shaft portion and positioned in the third type of hole.

In still other embodiments, the system comprises a bone plate configured to engage the bone. The bone plate comprises an inferior end having a base portion. The base portion has a first plurality of holes formed therethrough. A superior end has a shaft portion. The shaft portion has a second plurality of holes formed therethrough. The shaft portion also has an undercut contact surface and a plurality of side relief cuts formed therein between adjacent holes of the second plurality of holes. At least one fastener is received in the base portion and is positioned one of the first plurality of holes. At least one additional fastener is received in the shaft portion and positioned in one of the second plurality of holes.

Also provided are stabilization systems, methods for installing the stabilization systems, and kits including bone plates, fasteners, and components and instruments for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1 is a side elevational view of a bone plate assembly in accordance with some embodiments attached to a tibia.

FIG. 2 is a sectional view of an inferior end of a tibia and fibula.

FIG. 2A perspective view of a tibia and fibula and associated ligaments.

FIG. 13 is a top perspective view of an alternative bone plate in accordance with some embodiments.

FIG. 14 is a top perspective view of a locking bone plate through hole in accordance with some embodiments.

FIG. 15 is a top perspective view of a polyaxial bone plate through hole in accordance with some embodiments.

FIG. 16 is a front perspective view of an alternative bone plate assembly in accordance with some embodiments attached to a tibia.

FIG. 17 is a front elevational view of the bone plate assembly of FIG. 16.

FIG. 20 is a rear elevational view of the base portion of the bone plate assembly of FIG. 16.

FIG. 21 is a side elevational view of the bone plate assembly of FIG. 16.

FIG. 29 is a front elevational view of the bone plate assembly of FIG. 27.

FIG. 30 is a side elevational view of the bone plate assembly of FIG. 29.

FIG. 31 is an enlarged rear perspective view of a portion of the superior end of the bone plate of FIG. 29.

FIG. 32 is a sectional view of a bone with a screw inserted thereinto through a DCP slot in the bone plate of FIG. 27.

FIG. 34 is a front elevational view of an alternative bone plate in accordance with some embodiments.

FIG. 34A is a front elevational view of an alternative bone plate in accordance with some embodiments.

FIG. 34B is a front elevational view of an alternative bone plate in accordance with some embodiments.

FIG. 34C is a front elevational view of an alternative bone plate in accordance with some embodiments.

FIG. 34D is a front elevational view of an alternative bone plate in accordance with some embodiments.

FIG. 37 is a front elevational view of an alternative bone plate in accordance with some embodiments.

FIG. 38 is a side elevational view of the bone plate of FIG. 37.

DETAILED DESCRIPTION OF THE INVENTION

Figure 3:
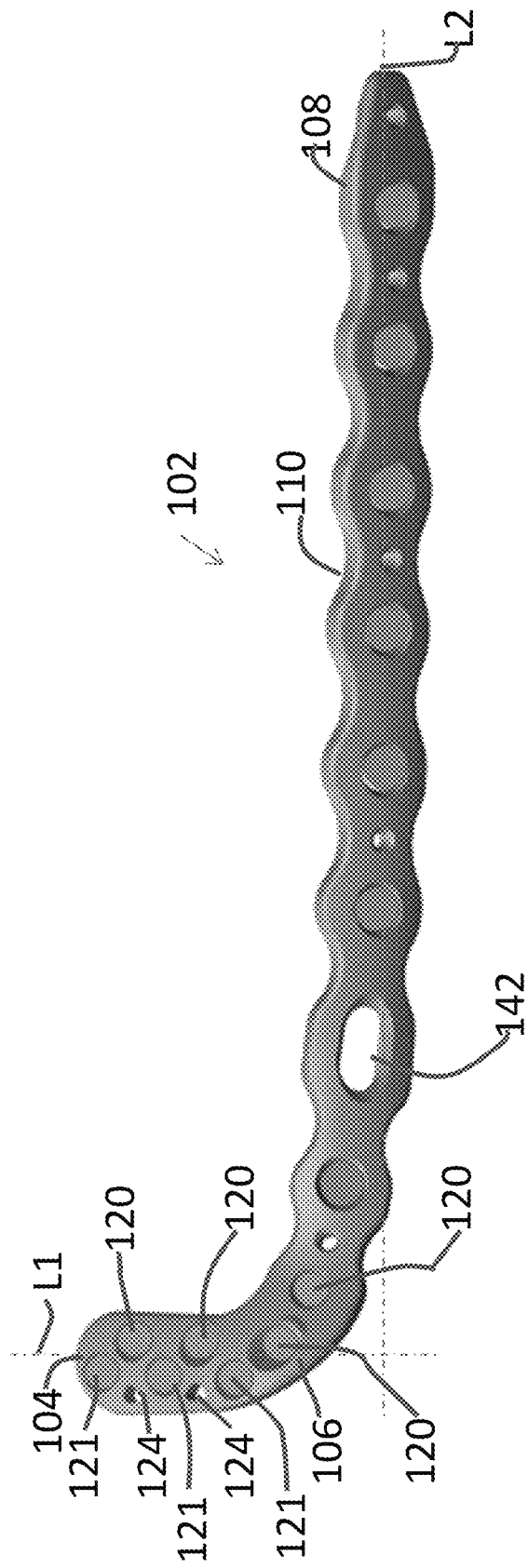
FIG. 3 is a side perspective view of the bone plate of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "superior" is defined as a direction toward an upper portion of a patient and "inferior" is defined as a direction toward a lower portion of the patient.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Embodiments of the present application are generally directed to devices, systems and methods for bone stabilization. In particular, embodiments are directed to bone plates that extend across bone members to treat one or more fractures.

The plates described herein may be adapted to contact one or more bones. For example, the plates may fit one more long bones, such as a femur, a distal tibia, a proximal tibia, a proximal humerus, a distal humerus, a clavicle, a fibula, an ulna, a radius, bones of the foot, bones of the hand, or other suitable bone or bones. The bone plates may be curved, contoured, straight, or flat. The plates may have a base portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

The bone plates can be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the bone plates may receive one or more screws or fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

Figure 6:
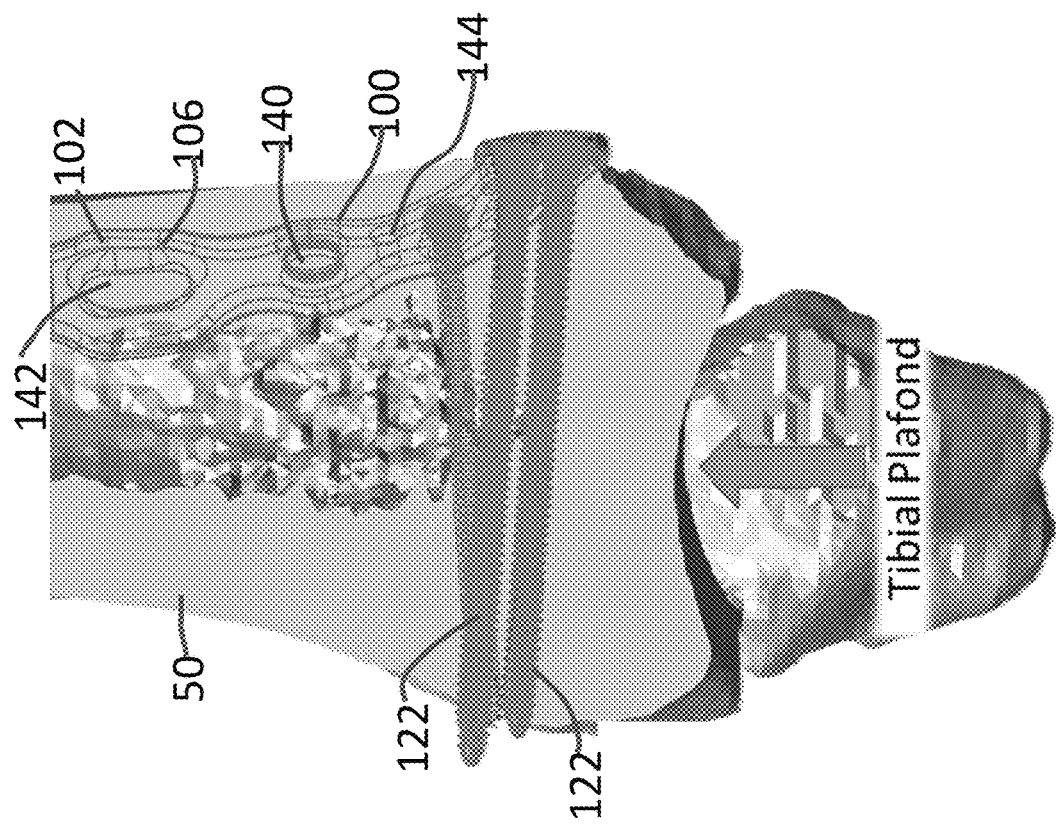
FIG. 6 is a perspective view of the inferior end of the bone plate of FIG. 3 with a plurality of screws inserted therethrough.

The bone plates described herein can be considered "locking" or "non-locking" plates. Locking plates include one or more openings for accepting one or more locking fasteners. The one or more openings can be partially or fully threaded. In some embodiments, these openings include fully threaded or stacked openings, which accept both locking and non-locking fasteners. In some embodiments, the locking fasteners include heads that are at least partially threaded. The locking fasteners can be monoaxial or polyaxial. One non-limiting example of a locking fastener (among others) is shown in FIG. 6 of U.S. Ser. No. 15/405,368, filed Jan. 13, 2017, which is hereby incorporated by reference in its entirety for all purposes.

Figure 4:
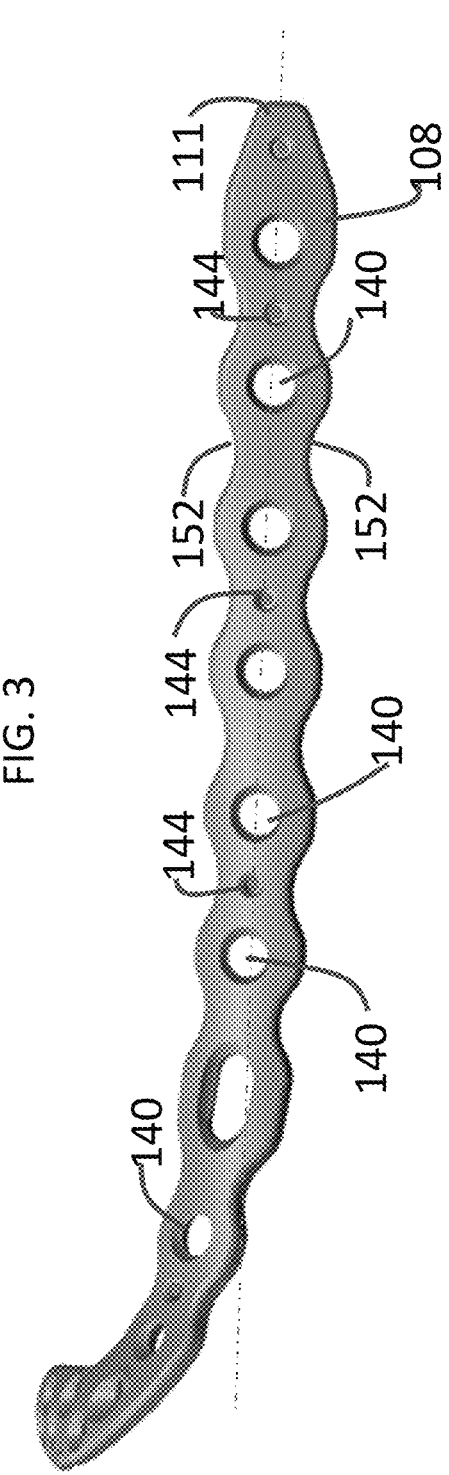
FIG. 4 is a front elevational view of the bone plate of FIG. 1.

Non-locking plates may include one or more openings for accepting one or more non-locking fasteners. The one or more openings at least in part are non-threaded. In some embodiments, these openings include non-threaded or stacked openings, which accept both locking and non-locking fasteners. In some embodiments, the non-locking fasteners include heads that are non-threaded. The non-locking fasteners can be monoaxial or polyaxial. One non-limiting example of a non-locking fastener (among others) is shown in FIG. 4 of U.S. Ser. No. 15/405,368, filed Jan. 13, 2017, which is hereby incorporated by reference in its entirety for all purposes. In some embodiments, the non-locking fasteners can include dynamic compression screws, which enable dynamic compression of an underlying bone.

Below are various examples of locking and non-locking plates attachable to bone. In some embodiments, locking plates may be thicker than non-locking plates. Locking plates may be useful for patients that have weaker bone, while non-locking plates may be useful for patients that have strong bone.

The locking and non-locking plates described below can be attached to different bones to treat fractures. In particular, the locking and non-locking plates can be used to treat fractures of the tibia, although one skilled in the art will appreciate that the novel plates described herein can be applied to fractures on other types of bone as well. Implants with anatomic shapes suitable for fixation at distinct regions of the tibia include anterolateral plates, medial plates, posterior T-plates, metaphyseal plates, anterior plates, and posterolateral plates. In other words, the plates can be attached to the above recited aspects of a tibia. One skilled in the art will appreciate, however, that the plates are not limited to their specific locations on the tibia, and that a surgeon may choose to, for example, apply a lateral plate distally or a distal plate laterally, if desired, and according to the anatomy of a particular patient.

FIGS. 1 and 3-15 disclose an anterolateral bone plate system 100 ("system 100") in accordance with a first embodiment. Referring to FIGS. 1-2A, system 100 is attached to a tibia 50 and is contoured to fit along the anterior-lateral portion of the tibia 50 along the syndesmosis 52 and the interosseous ligament 54 and extend onto the anterior portion of the tibia 50 (FIG. 1). The syndesmosis is a ligamentous attachment between the fibula 56 and the tibia 50 (See FIGS. 2 and 2A). An anterolateral bone plate 102 of system 100 is specific to the left and right tibia.

Referring to FIGS. 3 and 4, the bone plate 102 has a plurality of through holes formed therein for receiving fasteners, wherein at least some of the fasteners received therein are locking fasteners. The bone plate 102 comprises an inferior end 104 having a base portion 106 and a superior end 108 having a shaft portion 110. The bone plate 102 is multi-planar, with the shaft portion 110 extending generally in a singular plane, while the base portion 106 is curved away from the plane and extends across more than one plane. The curvature of the base portion 106 relative to the shaft portion 110 can be adjusted to match the anatomy of a particular patient.

The base portion 106 extends along a first longitudinal axis L1. In some embodiments, the inferior end 104 is chamfered around its perimeter. Advantageously, the contour and chamfer of the inferior end 104 helps to position the bone plate 102 to minimize soft tissue irritation. In some embodiments, the base portion 106 will be placed on a bone member (e.g., tibia) near an articular surface. Certain features of the base portion 106 are advantageously designed to prevent or resist subsidence of an articular surface.

Figure 5:
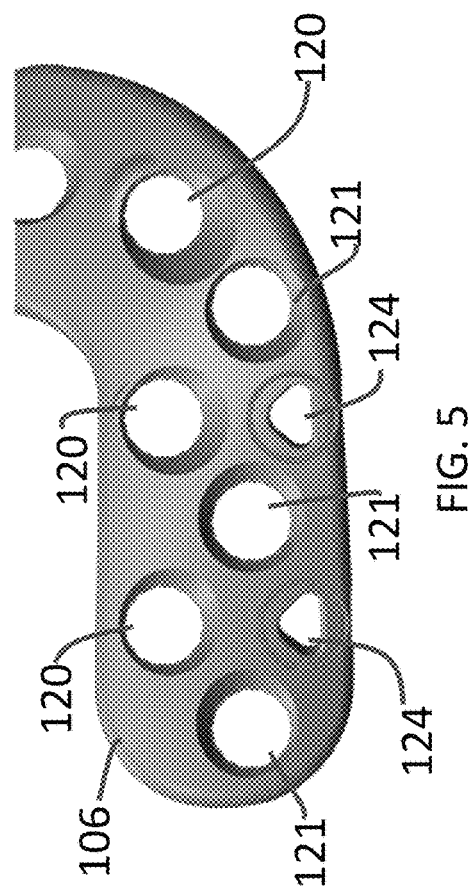
FIG. 5 is an enlarged front elevational view of an inferior end of the bone plate of FIG. 3.
Figure 7:
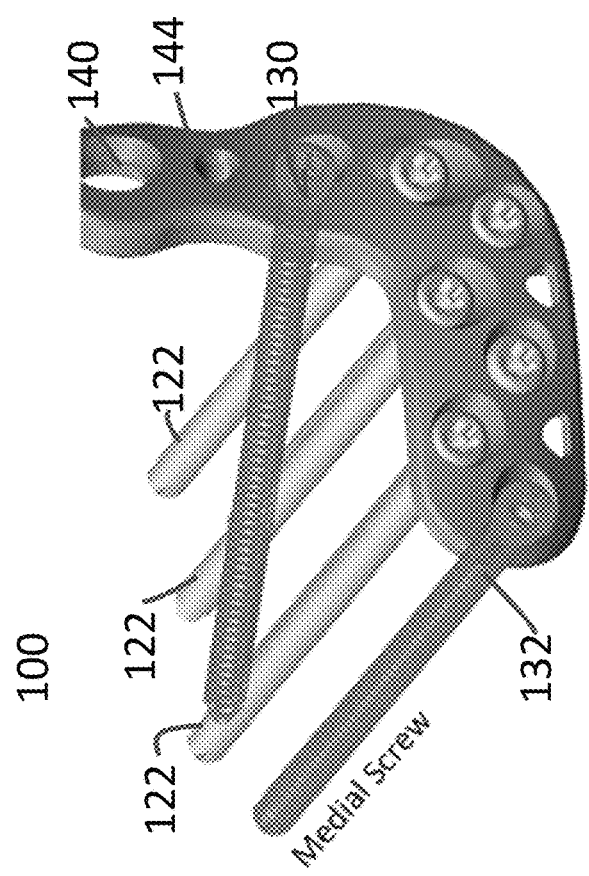
FIG. 7 is a sectional view of tibia with the bone plate of FIG. 1 attached thereto.

In an exemplary embodiment, as shown in FIGS. 5 and 6, the base portion 106 features two (2) rows of three (3) 2.5 mm polyaxial screw holes 120, 121. These holes 120, 121 are through holes for receiving rafting screws 122 that are closest to an articular surface of a joint. The purpose of these screws 122 is to capture articular fragments and provide a rafting construct. The nominal screw trajectories are parallel to the tibial plafond (joint surface) and support the articular fragments to maintain their alignment and rotation relative to the shaft of the tibia 50, as shown in FIG. 7.

By providing two sets of holes 120, 121, the bone plate 102 advantageously accommodates a greater number of rafting screws 122, thereby providing greater support near the joint. In some embodiments, the first row of holes 120 are offset from the second row of holes 121, while in other embodiments, the first row of holes 120 are aligned with the second row of holes 121. In some embodiments, the first row of holes 120 can have the same number of holes as the second row of holes 121, while in other embodiments, the first row of holes 120 can have a different number of holes than the second row of holes 121. In the present embodiment, the bone plate 102 includes three (3) holes 120 and three (3) holes 121.

Figure 8:
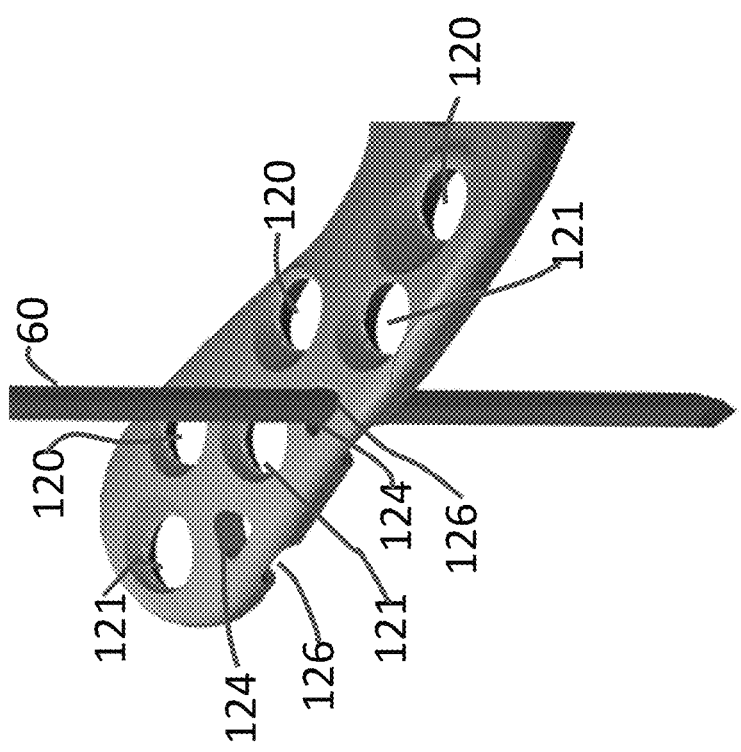
FIG. 8 is a perspective view of the inferior end of the bone plate of FIG. 3 with a K-wire inserted therethrough.

As shown in FIGS. 3 and 5, the most inferior edge of the base portion 106 further comprises one or more novel multi-purpose holes 124. The multi-purpose holes 124 are smaller than the holes 120, 121. In some embodiments, the multi-purpose holes 124 enable passage of suture/needles to serve as anchor points useful for reattachment and repositioning of soft tissue damaged during surgery. This may aid post-surgical soft tissue healing. The multi-purpose holes 124 also allow for a non-threaded 1.6 mm K-wire 60 to be provisionally placed, as shown in FIG. 8. As shown in FIG. 8, one or more undercuts 126 advantageously allow access to one or more sutures through the bone plate 102 even after the bone plate 102 is implanted on bone. The sutures can be used to attach the bone plate 102 to adjacent tissue, thereby further securing the bone plate 102 at or near a surgical site.

Additionally, referring to FIG. 6, the plate 102 features a single kickstand screw 130 that is angled towards the tip of the most medial screw 132. The purpose of the kickstand screw 130 is to provide additional stability of the articular fragments and aid in axial loading of the tibia 50.

Referring back to FIGS. 3 and 4, the shaft portion 110 is connected to the base portion 106. The shaft portion 110 extends along a second axis L2, different from the first axis L1. A plurality of polyaxial through holes 140 extend along the length of the shaft portion 110 and accept locking and non-locking screws, both inserted within a cone of angulation. At least four (4) holes 140 are provided and are sized to accept 3.5 mm screws.

The most superior portion of the shaft portion 110 further comprises a tapered tip 111. In some embodiments, the tapered tip 111 serves as an insertion tip that allows the plate 102 to be inserted beneath skin to a surgical site. The bone plate 102 can be positioned adjacent to bone (e.g., a tibia), whereby the plate 102 can be fixed to the bone. In some embodiments, the tapered tip 111 allows for simplified submuscular plate insertion to minimize incision length.

Figure 9:
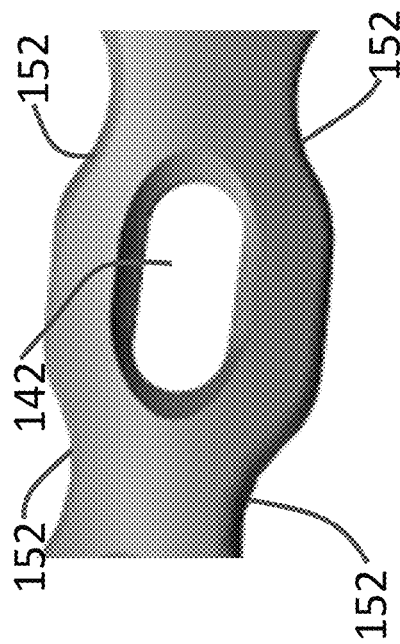
FIG. 9 is an enlarged top plan view of a portion of the superior end of the bone plate of FIG. 1 showing a dynamic compression plating ("DCP") slot.
Figure 10:
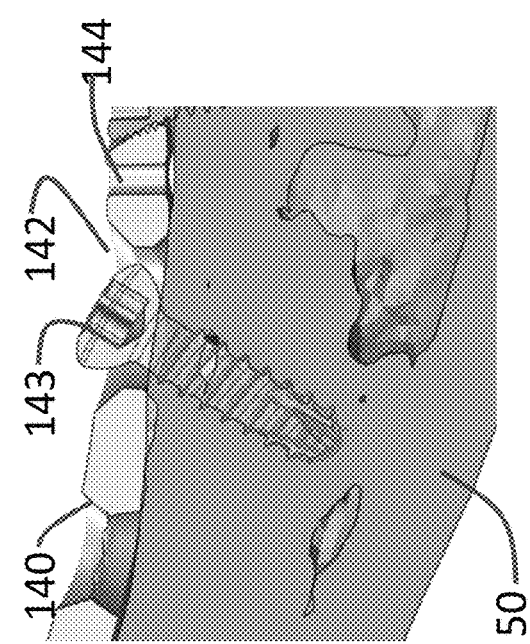
FIG. 10 is a sectional view of a bone with a screw inserted thereinto through the DCP slot of FIG. 9.

As shown in FIGS. 9 and 10, a dynamic compression plating ("DCP") slot 142 allows lateral motion of the plate 102 relative to the bone to compress a bone fracture. 3.5 mm non-locking screws 143 are used for this technique as well as standard neutral placement in the center of the slot 142. The DCP slot 142 is a through hole that also enables off-axis, or oblique, screw trajectories in the plane of the slot using 3.5 mm non-locking screws 143, as shown in FIG. 10. Alternatively, 4.0 mm cancellous screws enable oblique or neutral screw trajectories through the DCP slot 142, which can be useful for fragment capture or load neutralization across the fracture line. In some embodiments, the DCP slot 142 has a length that is greater than a length of any of the other holes 120, 121, 140 that receive bone screws therein. In some embodiments, the DCP slot 142 has a length that is at least twice the length of a length of any of the other holes 120, 121, 140 that receive bone screws therein.

K-wire through holes 144 are placed along the length of the plate 102, typically on either side of a through hole 140, to provide provisional fixation. The holes 144 allow for a 1.6 mm K-wire to be placed provisionally.

Figure 11:
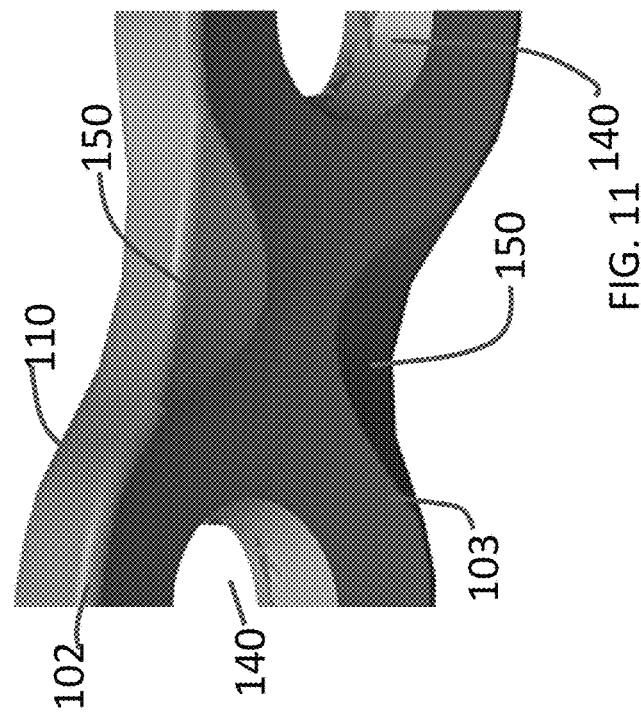
FIG. 11 is an enlarged rear perspective view of a portion of the superior end of the bone plate of FIG. 1.

Referring to FIG. 11, cylindrical undercuts 150 are formed on the rear surface 103 of the plate 102 between adjacent screw holes 140 to help reduce the moment of inertia between adjacent screw holes 140 to allow preferential bending between the holes 140, thereby helping to minimize deformation of the screw holes 140. This feature is useful for contour customization of the plate 102. In some embodiments, the undercuts 150 minimize impact to the periosteal blood supply.

Figure 12:
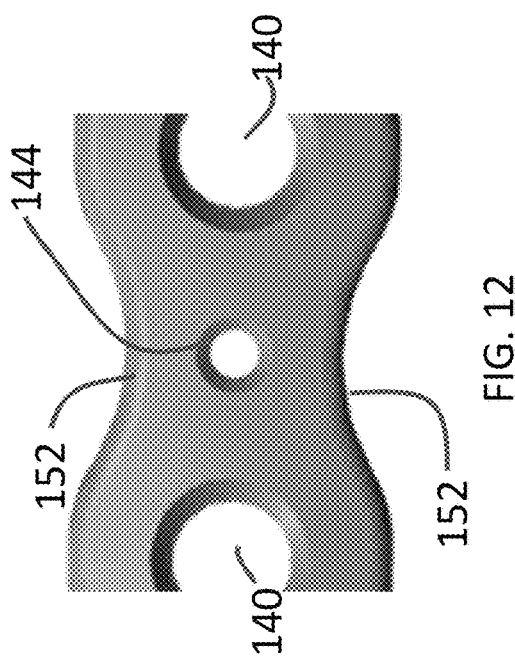
FIG. 12 is an enlarged front elevational view of a portion of the superior end of the bone plate of FIG. 1 showing a K-wire slot.

Side relief cuts, or bending scallops 152, shown in FIGS. 4 and 12, are provided in the sides of the plate 102 on either side of the longitudinal axis L2 and are another means of reducing the moment of inertia between screw holes 140 to allow preferential bending between the screw holes 140, helping to minimize deformation of the screw holes 140. The bending scallops 152 are present along the shaft portion 110 where contour customization by bending the plate 102 is the most likely to be desired.

While bone plate 102 is shown having two row of through holes 120, 121, those skilled in the art will recognize that a bone plate 102A, shown in FIG. 13, can include only a single row of through holes 120. Further, as shown in FIGS. 14 and 15, the through holes 120, 121, 140 in plates 102/102A can be threaded (FIG. 14) to accept threaded locking fasteners or unthreaded (FIG. 15) to accept polyaxial screws. Additionally, the through holes 120, 121 can be 2.5 mm or 3.5 mm in diameter, while the through holes 140 are typically 3.5 mm in diameter, although other suitable dimensions may be contemplated.

Figure 19:
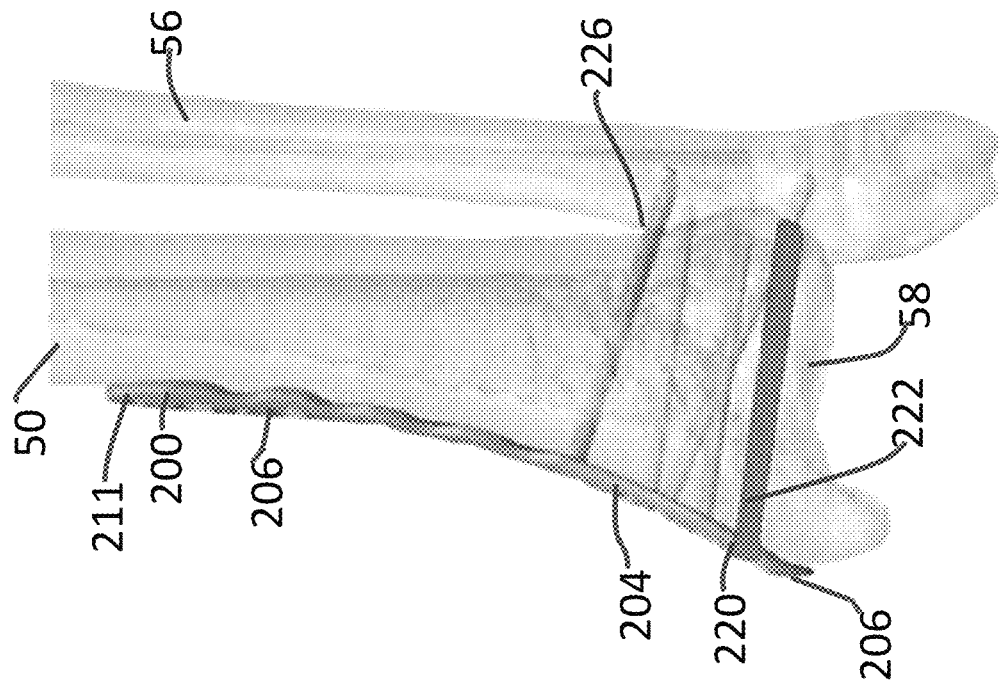
FIG. 19 us a side elevational view of the bone plate assembly and tibia of FIG. 16.
Figure 18:
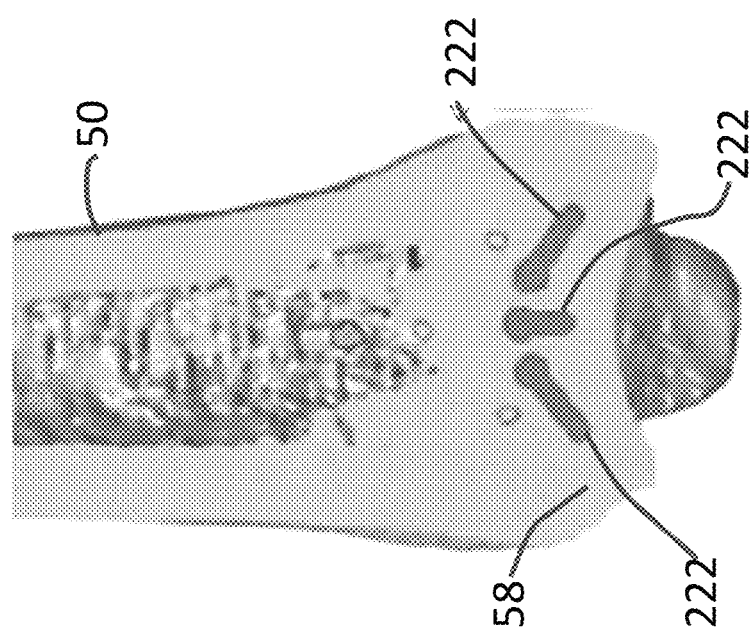
FIG. 18 is a sectional view of the inferior portion of the tibia of FIG. 16, showing screws from the bone plate assembly of FIG. 17.

FIGS. 16-26 disclose a bone plate system 200 ("system 200") in accordance with a second embodiment. System 200 includes a medial bone plate 202 that is contoured to fit along the medial portion of the tibia 50 (FIGS. 16 and 19). Bone plate 202 of system 200 is specific to the left and right tibia. The medial distal tibia 50 is an area of little soft tissue coverage and is by far one of the most challenging areas to treat pilon fractures from. The thickness of the plate 202 is minimal to reduce soft tissue irritation and failure.

Referring to FIG. 17 the bone plate 202 has a plurality of through holes formed therein for receiving fasteners, wherein at least some of the fasteners received therein are locking fasteners. The bone plate 202 comprises an inferior end 204 having a base portion 206 and a superior end 208 having a shaft portion 210. The bone plate 202 has a curvature as shown in FIG. 19, to accommodate the curvature of the inferior end of the tibia 50.

The body 202 extends along a longitudinal axis L3. In some embodiments, the inferior end 204 is chamfered around its perimeter. Advantageously, the contour and chamfer of the inferior end 204 helps to position the bone plate 202 to minimize soft tissue irritation. In some embodiments, the base portion 206 will be placed on a bone member (e.g., tibia) near an articular surface. Certain features of the base portion 206 are advantageously designed to prevent or resist subsidence of an articular surface. The base portion 206 is the widest portion of the plate 202.

In an exemplary embodiment, as shown in FIG. 17, the base portion 206 features a plurality of screw holes 220. The three (3) most inferior screw holes 220 accommodate polyaxial screws 222 and are oriented such that the screws 222 match the contour of the talar dome 58, also known as the plafond. See FIG. 18.

The remaining distal screws 224 diverge from each other to increase the working width of the plate 202, as shown in FIG. 20. This feature is beneficial for capturing both anterior bone fragments as well as posterior fragments, providing support to the articular block.

Referring to FIG. 20, the two outer most superior screws 224 are angled in an inferior direction to provide additional support of the articular block. The screws 224 also provide support for axial loading. In an exemplary embodiment, screw holes 220 are sized to accept 2.5 mm screws 222, 224.

Referring to FIGS. 20 and 21, the first screw hole 240 on the shaft portion 210 of the plate 202 closest to the base portion 206 supports a kickstand screw 226. The kickstand screw 226 crosses the fracture line of the tibia 50 and helps connect the articular block to the shaft of the tibia 50. In an exemplary embodiment, the screw holes 240 are sized to accept a 3.5 mm screw 226.

Referring back to FIG. 17, the shaft portion 210 is connected to the base portion 206 along axis L3. A plurality of polyaxial through holes 240 extend along the length of the shaft portion 210 and accept locking and non-locking screws, both inserted within a cone of angulation. At least four holes 240 are provided and are sized to accept 3.5 mm screws.

The most superior portion of the shaft portion 210 further comprises a tapered tip 211. In some embodiments, the tapered tip 211 serves as an insertion tip that allows the plate 202 to be inserted beneath skin to a surgical site. The bone plate 202 can be positioned adjacent to bone (e.g., a tibia), whereby the plate 202 can be fixed to the bone. In some embodiments, the tapered tip 211 allows for simplified submuscular plate insertion to minimize incision length.

Figure 22:
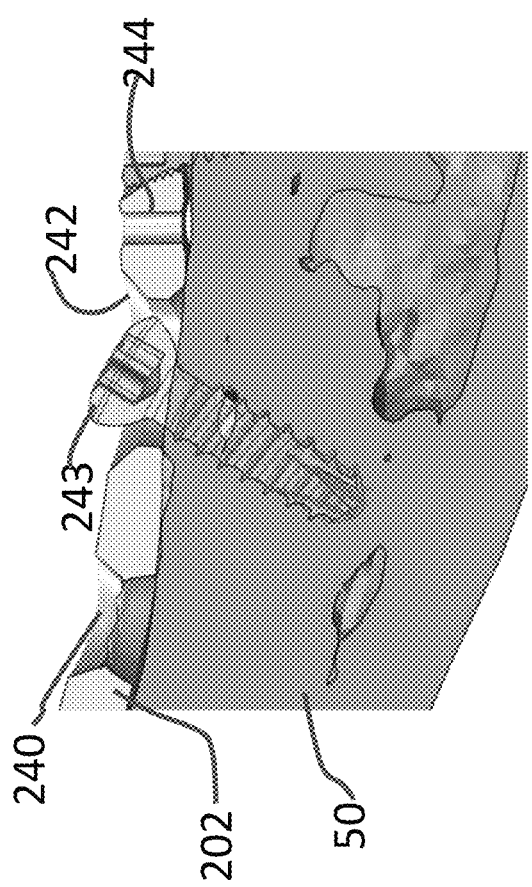
FIG. 22 is a sectional view of a bone with a screw inserted thereinto through a DCP slot in the bone plate of FIG. 16.

As shown in FIGS. 17 and 22, a dynamic compression plating ("DCP") slot 242 allows lateral motion of the plate 202 relative to the bone to compress a bone fracture. The DCP slot 242 is a through hole that also enables off-axis, or oblique, screw trajectories in the plane of the slot using 3.5 mm non-locking screws 243. Alternatively, 4.0 mm cancellous screws enable oblique or neutral screw trajectories through the DCP slot 242, which can be useful for fragment capture or load neutralization across the fracture line. In some embodiments, the DCP slot 242 has a length that is greater than a length of any of the other holes 220, 240 that receive bone screws therein. In some embodiments, the DCP slot 242 has a length that is at least twice the length of a length of any of the other holes 240, 242 that receive bone screws therein.

K-wire through holes 244 are placed along the length of the plate 202, typically on either side of a through hole 240, to provide provisional fixation. The holes 244 allow for a 1.6 mm K-wire to be placed provisionally.

Figure 23:
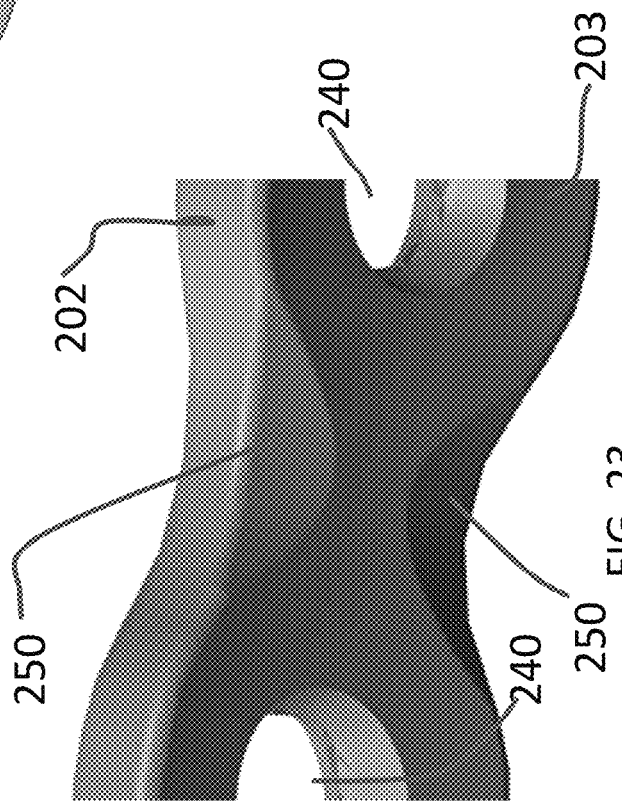
FIG. 23 is an enlarged rear perspective view of a portion of the superior end of the bone plate of FIG. 16.

Referring to FIG. 23, cylindrical undercuts 250 are formed on the rear surface 203 of the plate 202 between adjacent screw holes 240 to help reduce the moment of inertia between adjacent screw holes 240 to allow preferential bending between the holes 240, thereby helping to minimize deformation of the screw holes 240. This feature is useful for contour customization of the plate 202. In some embodiments, the undercuts 250 minimize impact to the periosteal blood supply.

Figure 24:
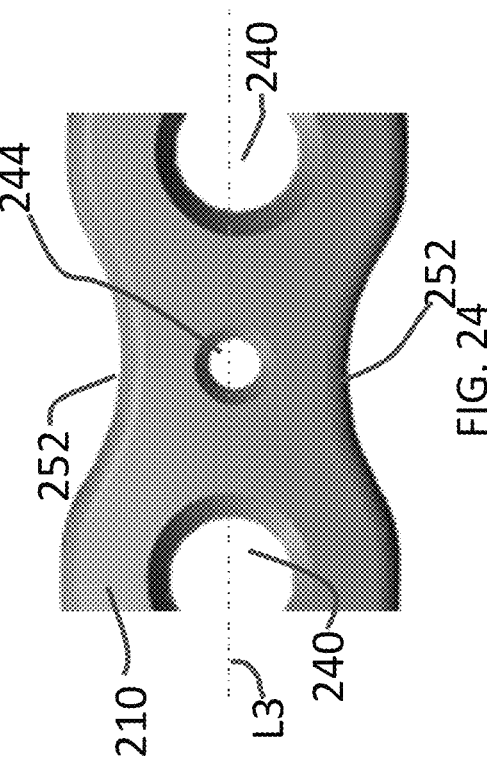
FIG. 24 is a front elevational view of a portion of the superior end of the bone plate of FIG. 16 showing a K-wire slot.

Side relief cuts, or bending scallops 252, shown in FIG. 24, are provided in the sides of the plate 202 on either side of the longitudinal axis L3 and are another means of reducing the moment of inertia between screw holes 240 to allow preferential bending between the screw holes 240, helping to minimize deformation of the screw holes 240. The bending scallops 252 are present along the shaft portion 210 where contour customization by bending the plate 202 is the most likely to be desired.

Figure 25:
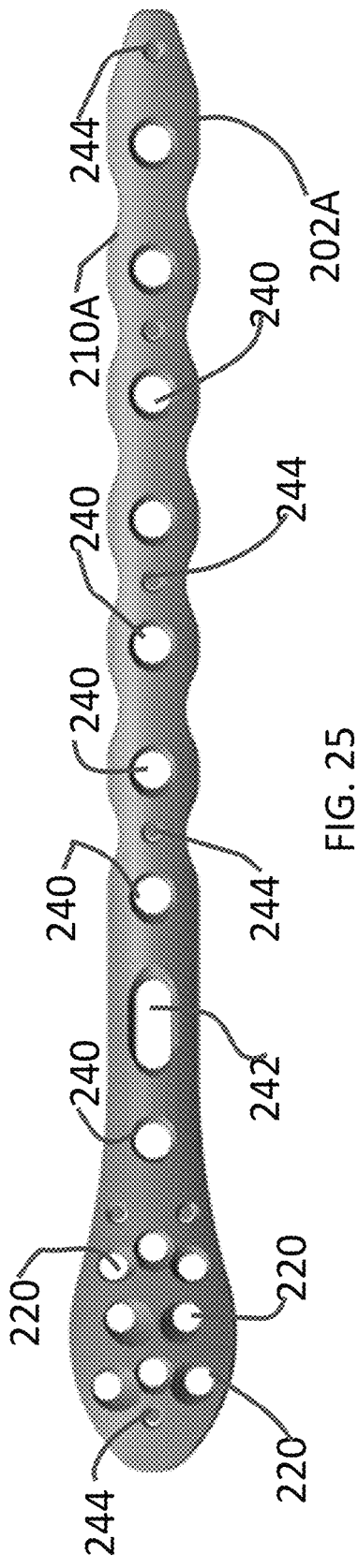
FIG. 25 is a front elevational view of an alternative bone plate in accordance with some embodiments.

While FIG. 17 shows the plate 202 having four (4) through holes 240 extending along the shaft portion 210, for larger patients, a plate 202A, shown in FIG. 25, can be used. The plate 202A has a longer shaft portion 210A than the shaft portion 210, and includes eight through holes 240, instead of the four (4) through holes 240 in the shaft portion 210. The shaft portion 210A also has a single DCP slot 242.

Figure 26:
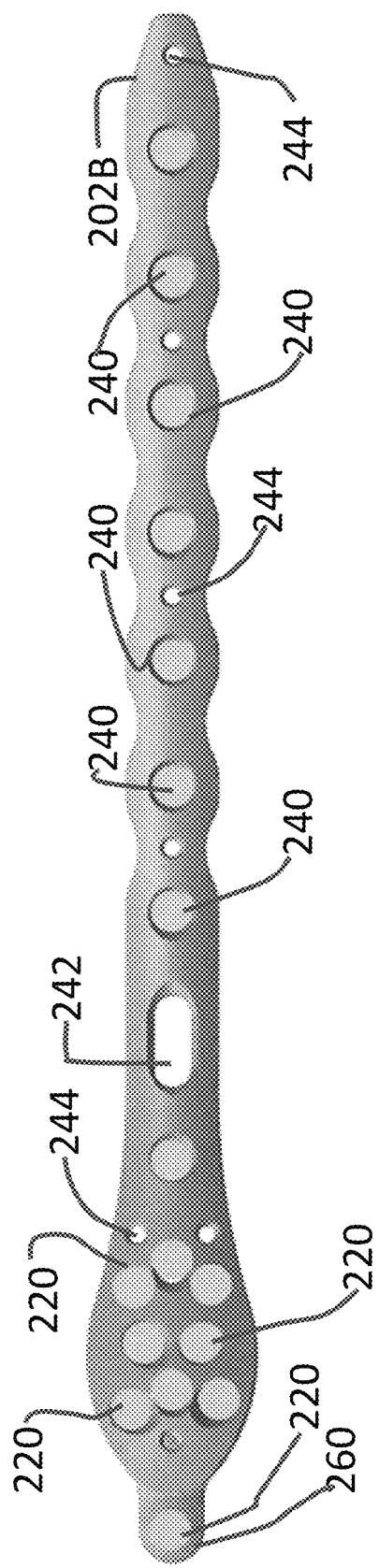
FIG. 26 is a front elevational view of an alternative bone plate in accordance with some embodiments.

FIG. 26 shows an alternative plate 202B that includes a medial malleolus tab 260 that extends inferiorly of the base portion 206. The medial malleolus tab 260 includes a through hole 240 formed therein.

Similar to the through holes 120, 121, 140 in the plate 102 discussed above, the through holes 220, 240 in the plate 202 can be threaded (see FIG. 14) to accept threaded locking fasteners or unthreaded (see FIG. 15) to accept polyaxial screws. Additionally, the through holes 220 can be 2.5 mm or 3.5 mm in diameter, while the through holes 240 are typically 3.5 mm in diameter.

Figure 28:
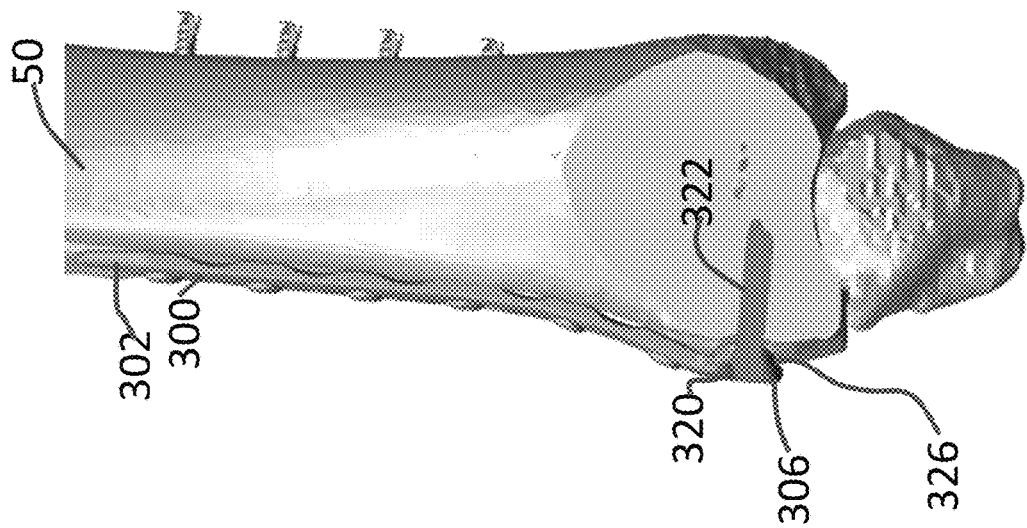
FIG. 28 is a side elevational view of the bone assembly and tibia, partially in section, of FIG. 27.
Figure 27:
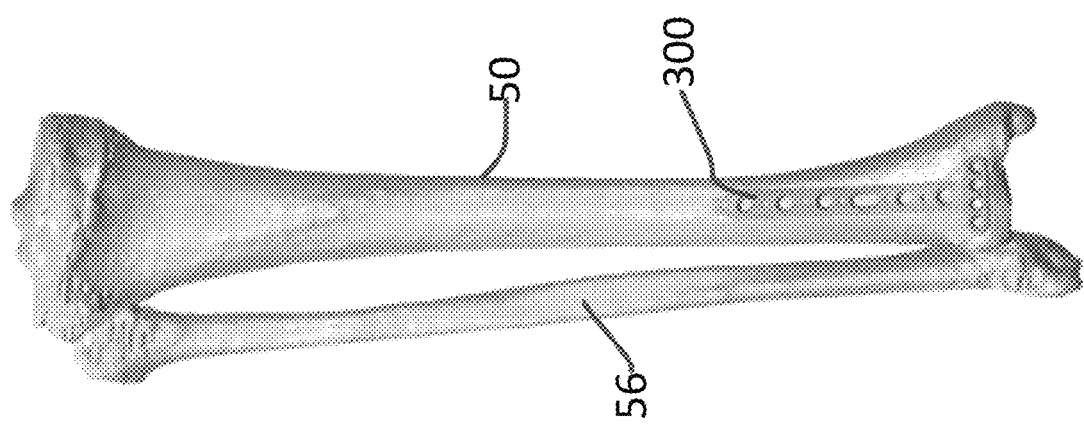
FIG. 27 front elevational view of an alternative bone plate assembly in accordance with some embodiments attached to a tibia.

FIGS. 27-33 disclose a bone plate system 300 ("system 300") in accordance with a third embodiment. System 300 includes a posterior bone plate 302 that is contoured to fit along the posterior portion of the tibia 50 (FIGS. 27 and 28). Bone plate 302 of system 300 is interchangeable for left-leg and right-leg tibias 50.

Referring to FIGS. 29 and 30, the bone plate 302 has a plurality of through holes formed therein for receiving fasteners, wherein at least some of the fasteners received therein are locking fasteners. The bone plate 302 comprises an inferior end 304 having a base portion 306 and a superior end 308 having a shaft portion 310. As shown in FIG. 30, the bone plate 302 is multi-planar, with the most superior end of the shaft portion 310 extending generally in a singular plane, while the most inferior end of the shaft portion 310 is curved away from the plane and extends across more than one plane. The curvature of the most inferior end of the shaft portion 310 relative to the most superior end of the shaft portion 310 can be adjusted to match the anatomy of a particular patient.

The base portion 306 extends along a first longitudinal axis L4. In some embodiments, the inferior end 304 is chamfered around its perimeter. Advantageously, the contour and chamfer of the inferior end 304 helps to position the bone plate 302 to minimize soft tissue irritation. In some embodiments, the base portion 306 will be placed on a bone member (e.g., tibia) near an articular surface. Certain features of the base portion 306 are advantageously designed to prevent or resist subsidence of an articular surface.

In an exemplary embodiment, as shown in FIG. 29, the base portion 306 features a single row of four (4) 2.5 mm polyaxial screw holes 320. These holes 320 are through holes for receiving polyaxial screws 322 that are mostly commonly placed uni-cortical (See FIG. 28). The function of the screws 322 is to support the posterior malleolus fragments and provide a secure block to which to fasten the anterior fragments.

As shown in FIG. 29, the most inferior edge of the base portion 306 further comprises one or more novel multi-purpose holes 324. The multi-purpose holes 324 are smaller than the holes 320. In some embodiments, the multi-purpose holes 324 enable passage of suture/needles to serve as anchor points useful for reattachment and repositioning of soft tissue damaged during surgery. This may aid post-surgical soft tissue healing. The multi-purpose holes 324 also allow for a non-threaded 1.6 mm K-wire (not shown) to be provisionally placed. As shown in FIG. 28, one or more undercuts 326 advantageously allow access to one or more sutures through the bone plate 302 even after the bone plate 302 is implanted on bone. The sutures can be used to attach the bone plate 302 to adjacent tissue, thereby further securing the bone plate 302 at or near a surgical site.

Referring back to FIGS. 29 and 30, the shaft portion 310 is connected to the base portion 306. The shaft portion 310 extends along a second axis L5, extending generally orthogonally to the first axis L4. A plurality of polyaxial through holes 340 extend along the length of the shaft portion 310 and accept locking and non-locking screws, both inserted within a cone of angulation. At least six holes 340 are provided and are sized to accept 3.5 mm screws 341. Additionally, referring to FIG. 30, the plate system 300 features two kickstand screws 330 that cross the fracture line and help connect the articular block to the shaft. The kickstand screws 330 are located in the two most inferior holes 340 and are proximal to the base portion 306.

The most superior portion of the shaft portion 310 further comprises a tapered tip 311. In some embodiments, the tapered tip 311 serves as an insertion tip that allows the plate 302 to be inserted beneath skin to a surgical site. The bone plate 302 can be positioned adjacent to bone (e.g., a tibia), whereby the plate 302 can be fixed to the bone. In some embodiments, the tapered tip 311 allows for simplified submuscular plate insertion to minimize incision length.

As shown in FIGS. 29 and 32, a DCP slot 342 allows lateral motion of the plate 302 relative to the bone to compress a bone fracture. 3.5 mm non-locking screws 343 are used for this technique as well as standard neutral placement in the center of the slot 342. The DCP slot 342 is a through hole that also enables off-axis, or oblique, screw trajectories in the plane of the slot using 3.5 mm non-locking screws 343, as shown in FIG. 32. Alternatively, 4.0 mm cancellous screws enable oblique or neutral screw trajectories through the DCP slot 342, which can be useful for fragment capture or load neutralization across the fracture line. In some embodiments, the DCP slot 342 has a length that is greater than a length of any of the other holes 320, 340 that receive bone screws therein. In some embodiments, the DCP slot 342 has a length that is at least twice the length of a length of any of the other holes 320, 340 that receive bone screws therein.

K-wire through holes 344 are placed along the length of the shaft portion 310, typically on either side of a through hole 340, to provide provisional fixation. The holes 344 allow for a 1.6 mm K-wire to be placed provisionally.

Referring to FIG. 31, cylindrical undercuts 350 are formed on the rear surface 303 of the plate 302 between adjacent screw holes 340 to help reduce the moment of inertia between adjacent screw holes 340 to allow preferential bending between the holes 340, thereby helping to minimize deformation of the screw holes 340. This feature is useful for contour customization of the plate 302. In some embodiments, the undercuts 350 minimize impact to the periosteal blood supply.

Similar to the through holes 120, 121, 140 in the plate 102 discussed above, the through holes 320, 340 in the plate 302 can be threaded (see FIG. 14) to accept threaded locking fasteners or unthreaded (see FIG. 15) to accept polyaxial screws. Additionally, the through holes 320 can be 2.5 mm or 3.5 mm in diameter, while the through holes 340 are typically 3.5 mm in diameter.

Figure 33:
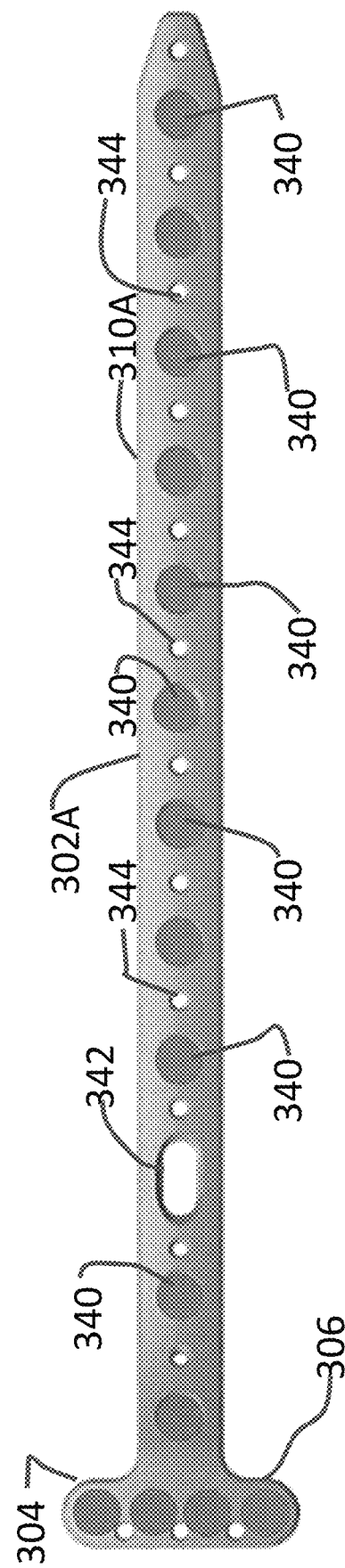
FIG. 33 is a front elevational view of an alternative bone plate in accordance with some embodiments.

While FIG. 29 shows the plate 302 having three through holes 340 extending along the shaft portion 210 superiorly of the DCP slot 342, for larger patients, a plate 302A, shown in FIG. 33, can be used. The plate 302A has a longer shaft portion 310A than the shaft portion 310, and includes nine through holes 340, instead of the four (4) through holes 340 in the shaft portion 310. The shaft portion 310A also has a single DCP slot 342.

Figure 36:
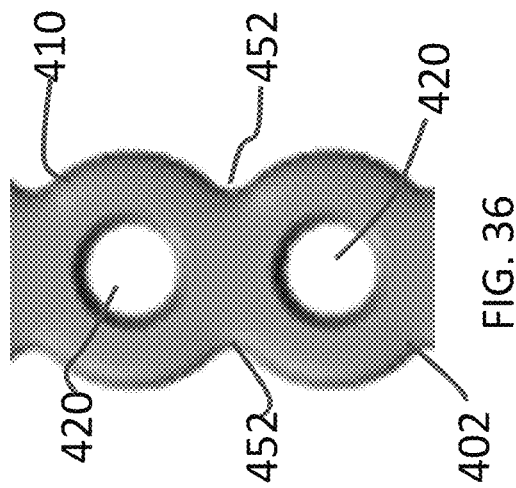
FIG. 36 is an enlarged front elevational view of is a portion of the inferior end of the bone plate of FIG. 34.
Figure 35:
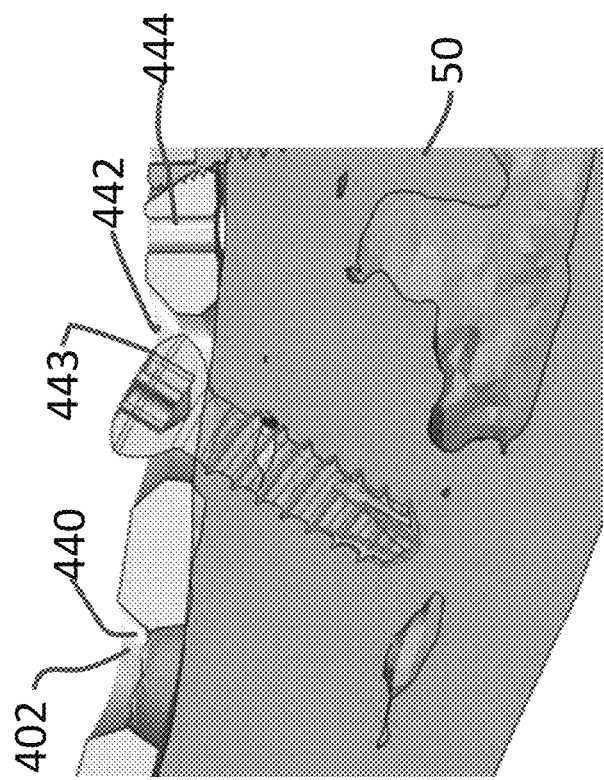
FIG. 35 is a sectional view of a bone with a screw inserted thereinto through a DCP slot in the bone plate of FIG. 34.

FIGS. 34-36 disclose a plurality of metaphyseal bone plates 402-402D in accordance with a fourth embodiment. FIGS. 34-34D show different embodiments of plates 402-402D with a common shaft portion 410, but with different base portions 406-406D.

The plates 402-402D are small and thin in required locations, specifically in the base portion 406-406D of the plates 402-402D. The plates 402-402D have a base portion 406-406D that has a smaller profile than the shaft portion 410 of the plates 402-402D. A benefit of the small profile and thin stock in the base portions 406-406D is the reduced risk of soft tissue irritation and soft tissue failure. The theory behind the plates 402-402D is a design that blends the small mini-fragment plates with the larger small fragment plates. The superior portion 410 is slightly thicker and wider than the inferior base portion 406, which provides the strength necessary to fix shaft fractures.

Referring to FIGS. 34-34D, the shaft portion 410 is connected to each of the different base portions 406-406D. The shaft portion 410 extends along a first axis L6. A plurality of polyaxial through holes 440 extend along the length of the shaft portion 410 and accept locking and non-locking screws, both inserted within a cone of angulation. At least two holes 440 are provided and are sized to accept 3.5 mm screws.

The most superior portion of the shaft portion 410 further comprises a tapered tip 411. In some embodiments, the tapered tip 411 serves as an insertion tip that allows the plate 402-402D to be inserted beneath skin to a surgical site. The bone plate 402-402D can be positioned adjacent to bone (e.g., a tibia), whereby the plate 402-402D can be fixed to the bone. In some embodiments, the tapered tip 411 allows for simplified submuscular plate insertion to minimize incision length.

As shown in FIGS. 34 and 35, a dynamic compression plating ("DCP") slot 442 allows lateral motion of the plate 402 relative to the bone to compress a bone fracture. 3.5 mm non-locking screws 443 are used for this technique as well as standard neutral placement in the center of the slot 442. The DCP slot 442 is a through hole that also enables off-axis, or oblique, screw trajectories in the plane of the slot using 3.5 mm non-locking screws 443, as shown in FIG. 35. Alternatively, 4.0 mm cancellous screws enable oblique or neutral screw trajectories through the DCP slot 442, which can be useful for fragment capture or load neutralization across the fracture line. In some embodiments, the DCP slot 442 has a length that is greater than a length of any of the other holes 420, 440 that receive bone screws therein. In some embodiments, the DCP slot 442 has a length that is at least twice the length of a length of any of the other holes 420, 440 that receive bone screws therein.

K-wire through holes 444 are placed proximate to the tip 411 of the plate 402 as well as proximate to an interface between the shaft portion 410 and the base portion 406-406D, to provide provisional fixation. The holes 444 allow for a 1.6 mm K-wire to be placed provisionally.

Another design feature of the plates 402-402D is the ability to adjust and customize the contour of the base portion 410-410D to match any patient's anatomy. Perimeter scallops 452 aid in bending the plate without distorting the 2.5 mm polyaxial screw through holes 420. In an exemplary embodiment, the through holes 420 are spaced about 7.5 mm apart from adjacent through holes 420 which maximizes the amount of fixation distally.

The plates 402-402D are designed with various shapes/profiles in the base portion 406-406D to accommodate different implantation locations. Plate 402 is a linear plate, wherein the base portion 406 extends along the first axis L6 co-linearly with the shaft portion 410.

Plate 402A is a Y-plate, with a first leg 460 extending along a second axis L7, different from the first axis L6, and a second leg 462 extending along a third axis L8, different from the first axis L6, wherein each of the axes L7 and L8 each extend at an angle of about 30 degrees relative to the axis L6.

Plate 402B is also a Y-plate, with a first leg 460B extending along a second axis L9, different from the first axis L6, and a second leg 462B extending along a third axis L8, different from the first axis L6, wherein each of the axes L7 and L8 each extend at an angle of about 320 degrees relative to the axis L6.

Plate 402C is a T-plate, with a first leg 460C extending along a second axis L10, generally orthogonal to the first axis L6. Plate 402D is a clover plate, with a plurality of 2.5 mm polyaxial screw through holes 420 surrounding a central 2.5 mm polyaxial screw through hole 420.

Each plate 402-402D is optimal for different scenarios. For example, plates 402A, 402B are the perfect shape for the medial distal tibia. The two legs 460B, 462B and 460C, 462C of the Y can be bent to fit around the medial malleolus.

FIGS. 37 and 38 disclose an anterior bone plate 502 in accordance with a fifth embodiment. The plate 502 is designed to be placed anterior on the distal tibia (See FIG. 38) and is similar to the metaphyseal plates 402-402D discussed above in the sense that the plate 502 can be modified and customized to fit the anatomy of the anterior tibia. The anterior distal tibia lacks soft tissue coverage, similar to the medial distal tibia. The anterior plate 502 is thin, much like the medial bone plate 202 and the base portion 106 of the anterolateral plate 102.

The bone plate 502 comprises an inferior end 504 having a base portion 506 and a superior end 508 having a shaft portion 510. The bone plate 502 is generally planar, but can be contoured to match a particular patient's anatomy.

The base portion 506 is generally triangular in shape. In some embodiments, the inferior end 504 is chamfered around its perimeter. Advantageously, the contour and chamfer of the inferior end 504 helps to position the bone plate 502 to minimize soft tissue irritation. In some embodiments, the base portion 506 will be placed on a bone member (e.g., tibia) near an articular surface. Certain features of the base portion 506 are advantageously designed to prevent or resist subsidence of an articular surface.

In an exemplary embodiment, as shown in FIG. 37, the base portion 506 features two (2) rows of three (3) 3.5 mm screw holes 520, 521, each row extending along a respective leg 560, 562. The holes 520, 521 are through holes for receiving screws that are closest to an articular surface of a joint. The holes 520, 521 can be locking holes or polyaxial holes. The polyaxial holes accept locking and non-locking screws, both inserted within a cone of angulation. Each leg 560, 562 extends at an angle of about 15 degrees relative to a shaft longitudinal axis L12.

A connecting portion 564 connects the inferior most ends of the legs 560, 562 to each other. The connecting portion 564 includes a row of four (4) 2.5 mm polyaxial screw holes 524. A cavity 526 is provided between the legs 560, 562 and the connecting portion 564.

By providing three (3) sets of holes 520, 521, 524, the bone plate 502 advantageously accommodates a greater number of screws, thereby providing greater support near the joint.

The shaft portion 510 is connected to the base portion 506. The shaft portion 510 extends along the axis L12. A plurality of polyaxial through holes 540 extend along the length of the shaft portion 510 and accept locking and non-locking screws, both inserted within a cone of angulation. At least three (3) holes 540 are provided and are sized to accept 3.5 mm screws.

The most superior portion of the shaft portion 510 further comprises a tapered tip 511. In some embodiments, the tapered tip 511 serves as an insertion tip that allows the plate 502 to be inserted beneath skin to a surgical site. The bone plate 502 can be positioned adjacent to bone (e.g., a tibia), whereby the plate 502 can be fixed to the bone. In some embodiments, the tapered tip 511 allows for simplified submuscular plate insertion to minimize incision length.

Figure 40:
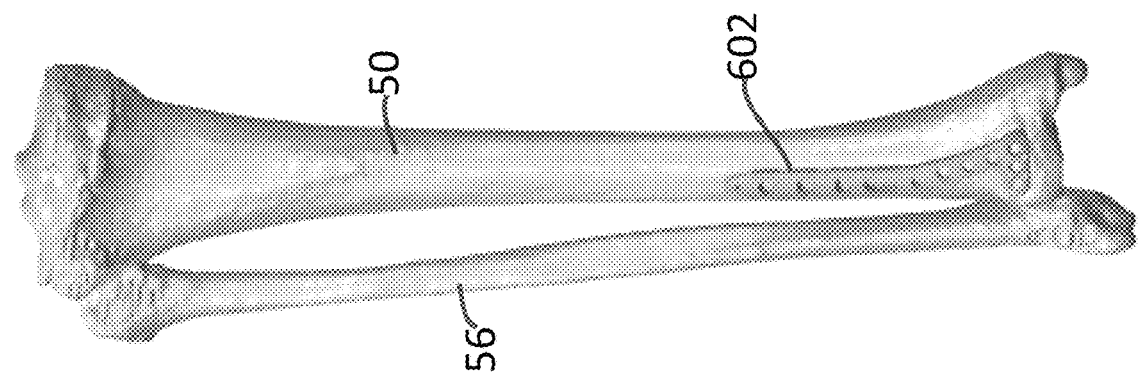
FIG. 40 is a front perspective view of the bone plate of FIG. 39 attached to a tibia.
Figure 39:
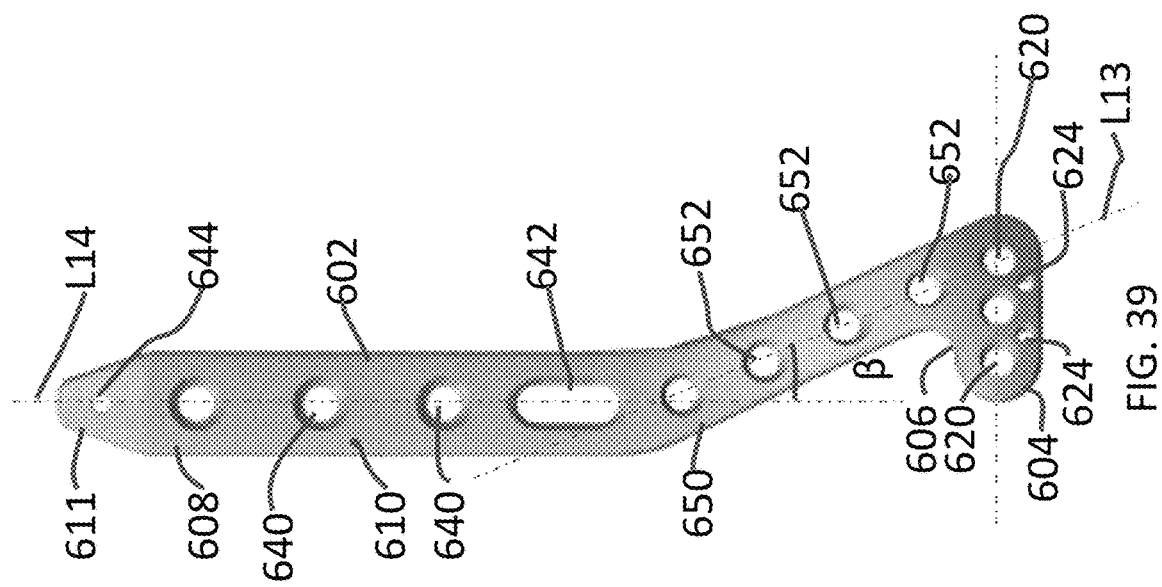
FIG. 39 is a front elevational view of an alternative bone plate in accordance with some embodiments.

FIGS. 39 and 40 disclose a posterolateral bone plate 602 in accordance with a sixth embodiment. The plate 602 is designed to address a posterior fracture of the tibia 50, as shown in FIG. 40.

Referring to FIG. 39, the bone plate 602 comprises an inferior end 604 having a base portion 606 and a superior end 608 having a shaft portion 610. The base portion 606 extends along a first longitudinal axis L13. In some embodiments, the inferior end 604 is chamfered around its perimeter. Advantageously, the contour and chamfer of the inferior end 604 helps to position the bone plate 602 to minimize soft tissue irritation. In some embodiments, the base portion 606 will be placed on a bone member (e.g., tibia 50) near an articular surface. Certain features of the base portion 606 are advantageously designed to prevent or resist subsidence of an articular surface.

In an exemplary embodiment, as shown in FIG. 39, the base portion 306 features a single row of three (3) 2.5 mm co-linear screw holes 620. The holes 620 are through holes for receiving screws that are closest to an articular surface of a joint. The holes 620 can be locking holes or polyaxial holes. The polyaxial holes accept locking and non-locking screws, both inserted within a cone of angulation.

The most inferior edge of the base portion 606 further comprises one or more novel multi-purpose holes 624. The multi-purpose holes 624 are smaller than the holes 620. In some embodiments, the multi-purpose holes 624 enable passage of suture/needles to serve as anchor points useful for reattachment and repositioning of soft tissue damaged during surgery. This may aid post-surgical soft tissue healing. The multi-purpose holes 624 also allow for a non-threaded 1.6 mm K-wire to be provisionally placed.

The shaft portion 610 is connected to the base portion 606. The shaft portion 610 extends along a second axis L14, different from the first axis L13. A plurality of polyaxial through holes 640 extend along the length of the shaft portion 610 and accept locking and non-locking screws, both inserted within a cone of angulation. At least three (3) holes 640 are provided and are sized to accept 3.5 mm screws.

The most superior portion of the shaft portion 610 further comprises a tapered tip 611. In some embodiments, the tapered tip 611 serves as an insertion tip that allows the plate 602 to be inserted beneath skin to a surgical site. The bone plate 602 can be positioned adjacent to bone (e.g., a tibia), whereby the plate 602 can be fixed to the bone. In some embodiments, the tapered tip 611 allows for simplified submuscular plate insertion to minimize incision length.

As shown in FIG. 39, a DCP slot 642 allows lateral motion of the plate 102 relative to the bone to compress a bone fracture. 3.5 mm non-locking screws (not shown) are used for this technique as well as standard neutral placement in the center of the slot 642. The DCP slot 642 is a through hole that also enables off-axis, or oblique, screw trajectories in the plane of the slot using 3.5 mm non-locking screws. Alternatively, 4.0 mm cancellous screws enable oblique or neutral screw trajectories through the DCP slot 642, which can be useful for fragment capture or load neutralization across the fracture line. In some embodiments, the DCP slot 642 has a length that is greater than a length of any of the other holes 620, 640 that receive bone screws therein. In some embodiments, the DCP slot 642 has a length that is at least twice the length of a length of any of the other holes 620, 640 that receive bone screws therein.

A K-wire through hole 644 is located at the superior end of the shaft portion 608, proximate to the tip 611, to provide provisional fixation. The hole 644 allows for a 1.6 mm K-wire to be placed provisionally.

An inferior part 650 of shaft portion 610 connects the DCP slot 642 to the base portion 606. Inferior part 650 is angled with respect to axis L13 by an angle β of about 22 degrees. Inferior part 650 includes a plurality of polyaxial through holes 652 extend along the length of the inferior part 650 and accept locking and non-locking screws, both inserted within a cone of angulation. At least three (3) holes 652 are provided and are sized to accept 2.5 mm screws. In the embodiment shown in FIG. 39, four (4) holes 652 are provided.

While some embodiments of plates 102-602 according to exemplary embodiments are shown with screws, while other plates 102-602 are not, those skilled in the art will recognize that all screw holes x20, x21, x40, x42 can include suitable screws of the screws described herein.

In accordance with one embodiment, a method of treating or fixing fractures and/or non-unions of the distal tibia may include providing one or more of the trauma plates to the affected region and securing the plate thereto. In particular, the method for repairing a bone fracture or non-union may include providing a bone plate or kit of bone plates having different sizes, shapes, or configurations, selecting the appropriate bone plate, positioning the bone plate adjacent to the affected area, and securing the bone plate to the bone or bone portions.

One skilled in the art will appreciate that the embodiments discussed above are non-limiting. While bone plates may be described as suitable for a particular approach (e.g., medial or posterior), one skilled in the art will appreciate that the bone plates can be used for multiple approaches. In addition, while bone plates are described as having particular holes (e.g., locking or non-locking), one skilled in the art will appreciate that any of the bone plates can include locking, non-locking or a combination of locking and non-locking holes. In addition to the bone plates, screws and instruments described above, one skilled in the art will appreciate that these described features can be used with a number of trauma treatment instruments and implants, including fixators, rods, and other plates and screws.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto. The feature or features of one embodiment may be wholly or partially incorporated into another embodiment without departing from the scope of the invention.

What is claimed is:

1. A medial plate for treating a fracture in a tibial bone comprising:
    a shaft adapted to be attached to a medial side of the tibial bone, the shaft disposed toward a superior end and defining a central longitudinal axis, the shaft having a first set of bone screw holes arranged along the central longitudinal axis;
    a base extending distally of the shaft and disposed at an inferior end, the base having a second set of bone screw holes arranged along the central longitudinal axis, the base further having a third set of bone screw holes laterally offset from the central longitudinal axis in a first direction and a fourth set of corresponding bone screw holes laterally offset from the central longitudinal axis in a second direction opposite from the first direction, wherein an inferiormost bone screw hole of the second set of bone screw holes, an inferiormost bone screw hole of the third set of bone screw holes, and an inferiormost bone screw hole of the fourth set of bone screw holes are each non-threaded and configured to receive a polyaxial screw and oriented such that the polyaxial screws match the contour of a talar dome of the tibial bone,
    where the base includes a series of cylindrical undercuts formed on a rear surface of the medial plate between adjacent screw holes to reduce moment of inertia between adjacent screw holes to allow preferential bending between the bone screw holes,
    wherein the base includes side relief cuts on the sides of the base, to allow additional bending of the base between screw holes.

2. The medial plate of claim 1, wherein the third set of bone screw holes is a mirror image of the fourth set of bone screw holes along the central longitudinal axis.

3. The medial plate of claim 1, wherein at least one of the bone screw holes of the first set of bone screw holes is a dynamic compression plating slot configured for receiving a non-locking bone screw.

4. The medial plate of claim 1, wherein at least one hole from the third set of bone screw holes and a corresponding bone screw hole from the fourth set are divergently oriented such that bone screw received therein diverge from each other to increase a working width of the plate.

5. The medial plate of claim 1, wherein at least two holes from the third set of bone screw holes and corresponding bone screw holes from the fourth set are divergently oriented such that bone screws received therein diverge from each other to increase a working width of the plate.

6. The medial plate of claim 1, wherein at least one hole in the first set is adapted to receive a kickstand screw.

7. The medial plate of claim 1, wherein the first set of bone screw holes are the only bone screw holes in the shaft.

8. The medial plate of claim 1, further comprising:
    a first k-wire hole disposed above the first set of bone screw holes; and
    a second k-wire hole disposed in between two of the first set of bone screw holes.

9. The medial plate of claim 8, wherein:
    one of the first set of holes is a dynamic compression plating slot configured for receiving a non-locking bone screw;
    the dynamic compression plating slot is disposed below the first and second k-wire holes.

10. The medial plate of claim 1, wherein the base includes a medial malleolus tab extending inferiorly and having a through-hole.

11. A medial plate for treating a fracture in a tibial bone comprising:
    a shaft adapted to be attached to a medial side of the tibial bone, the shaft disposed toward a superior end and defining a central longitudinal axis, the shaft having a first set of bone screw holes arranged along the central longitudinal axis, at least one of the first set including a dynamic compression plating slot for receiving a non-locking bone screw;
    a base extending distally of the shaft and disposed at an inferior end, the base having a second set of bone screw holes arranged along the central longitudinal axis, the base further having a third set of bone screw holes laterally offset from the central longitudinal axis in a first direction and a fourth set of corresponding bone screw holes laterally offset from the central longitudinal axis in a second direction opposite from the first direction such that the third set of bone screw holes is a mirror image of the fourth set of bone screw holes along the central longitudinal axis, wherein an inferiormost bone screw hole of the second set of bone screw holes, an inferiormost bone screw hole of the third set of bone screw holes, and an inferiormost bone screw hole of the fourth set of bone screw holes are each non-threaded and configured to receive a polyaxial screw and oriented such that the polyaxial screws match the contour of a talar dome of the tibial bone, where the base includes a series of cylindrical undercuts formed on a rear surface of the medial plate between adjacent screw holes to reduce moment of inertia between adjacent screw holes to allow preferential bending between the bone screw holes, wherein the base includes side relief cuts on the sides of the base, to allow additional bending of the base between screw holes.

12. The medial plate of claim 11, wherein at least one hole from the third set of bone screw holes and a corresponding bone screw hole from the fourth set are divergently oriented such that bone screws received therein diverge from each other to increase a working width of the plate.

13. The medial plate of claim 11, wherein at least two holes from the third set of bone screw holes and corresponding bone screw holes from the fourth set are divergently oriented such that bone screws received therein diverge from each other to increase a working width of the plate.

14. The medial plate of claim 11, wherein at least one hole in the first set is adapted to receive a kickstand screw.

15. The medial plate of claim 11, wherein the first set of bone screw holes are the only bone screw holes in the shaft.

16. The medial plate of claim 11, further comprising:
a first k-wire hole disposed above the first set of bone screw holes; and
a second k-wire hole disposed in between two of the first set of bone screw holes.

17. The medial plate of claim 16, wherein the dynamic compression plating slot is disposed below the first and second k-wire holes.

18. The medial plate of claim 11, wherein the base includes a medial malleolus tab extending inferiorly and having a through-hole.

* * * * *